(12) United States Patent
Bowden et al.

(10) Patent No.: US 10,070,894 B2
(45) Date of Patent: Sep. 11, 2018

(54) COMPLIANT VERTEBRAL ATTACHMENT DEVICE

(71) Applicant: BRIGHAM YOUNG UNIVERSITY, Provo, UT (US)

(72) Inventors: Anton E. Bowden, Lindon, UT (US); Aubrie Taylor, Provo, UT (US); Cassandra Bell, McKinney, TX (US)

(73) Assignee: Brigham Young University, Provo, UT (US)

( * ) Notice: Subject to any disclaimer, the term of this patent is extended or adjusted under 35 U.S.C. 154(b) by 0 days.

(21) Appl. No.: 15/006,490

(22) Filed: Jan. 26, 2016

(65) Prior Publication Data

US 2016/0213403 A1 Jul. 28, 2016

Related U.S. Application Data

(60) Provisional application No. 62/107,921, filed on Jan. 26, 2015.

(51) Int. Cl.
| | |
|---|---|
| *A61B 17/70* | (2006.01) |
| *A61B 17/84* | (2006.01) |
| *A61B 17/56* | (2006.01) |
| *A61B 17/80* | (2006.01) |

(52) U.S. Cl.
CPC .......... *A61B 17/70* (2013.01); *A61B 17/7044* (2013.01); *A61B 17/809* (2013.01); *A61B 17/8085* (2013.01); *A61B 2017/564* (2013.01)

(58) Field of Classification Search
CPC . A61B 17/70; A61B 17/7044; A61B 17/8085; A61B 17/809; A61B 2017/564

USPC .................. 606/246–279, 74, 281
See application file for complete search history.

(56) References Cited

U.S. PATENT DOCUMENTS

| 1,156,440 | A | * | 10/1915 | Smith | ..................... | A61B 17/80 |
| | | | | | | 606/70 |
| 2,494,792 | A | * | 1/1950 | Bloom | ................... | A61B 90/14 |
| | | | | | | 33/512 |
| 4,263,904 | A | * | 4/1981 | Judet | ...................... | A61B 17/68 |
| | | | | | | 606/281 |
| 5,015,248 | A | * | 5/1991 | Burstein | ................ | A61B 17/68 |
| | | | | | | 606/297 |
| 8,080,014 | B2 | * | 12/2011 | Roue | ................... | A61B 17/0401 |
| | | | | | | 606/99 |
| 2005/0177160 | A1 | | 8/2005 | Baynham et al. | | |
| 2007/0055250 | A1 | * | 3/2007 | Aflatoon | ............ | A61B 17/7059 |
| | | | | | | 606/86 A |
| 2008/0077141 | A1 | | 3/2008 | Bray | | |

(Continued)

OTHER PUBLICATIONS

Aebli et al., "In Vivo Temperature Profile of Intervertebral Discs and Vertebral Endplates During Vertebroplasty: An Experimental Study in Sheep", Spine (Phila Pa 1976), vol. 31, Issue 15, discussion 1679, Jul. 1, 2006, pp. 1674-1678.

(Continued)

*Primary Examiner* — Pedro Philogene
(74) *Attorney, Agent, or Firm* — Brake Hughes Bellermann LLP

(57) ABSTRACT

In one general aspect, a vertebral attachment device can include an attachment member having a curved shape defining a concave surface, a flex structure included in the attachment member, and an anchor member coupled to the attachment member and protruding from the concave surface.

23 Claims, 17 Drawing Sheets

(56) References Cited

U.S. PATENT DOCUMENTS

2012/0078305 A1    3/2012  Wang et al.
2012/0226320 A1*   9/2012  Kang ................. A61B 17/8076
                                                    606/283
2013/0190830 A1*   7/2013  Champagne ......... A61B 17/863
                                                    606/315

OTHER PUBLICATIONS

Belkoff et al., "An Ex Vivo Biomechanical Evaluation of a Hydroxyapatite Cement for Use with Vertebroplasty", Spine (Phila Pa 1976), vol. 26, Issue 14, Jul. 15, 2001, pp. 1542-1546.
Cappuccino et al., "Biomechanical Analysis and Review of Lateral Lumbar Fusion Constructs", Spine (Phila Pa 1976), vol. 35, Issue 26 Suppl., 2010, pp. S361-S367.
International Search Report and Written Opinion received for PCT Patent Application No. PCT/US2016/014845, dated Mar. 21, 2016, 10 pages.

* cited by examiner

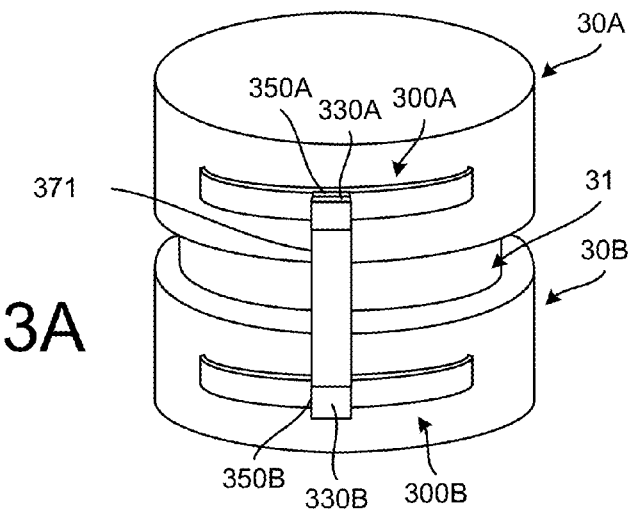
FIG. 3A
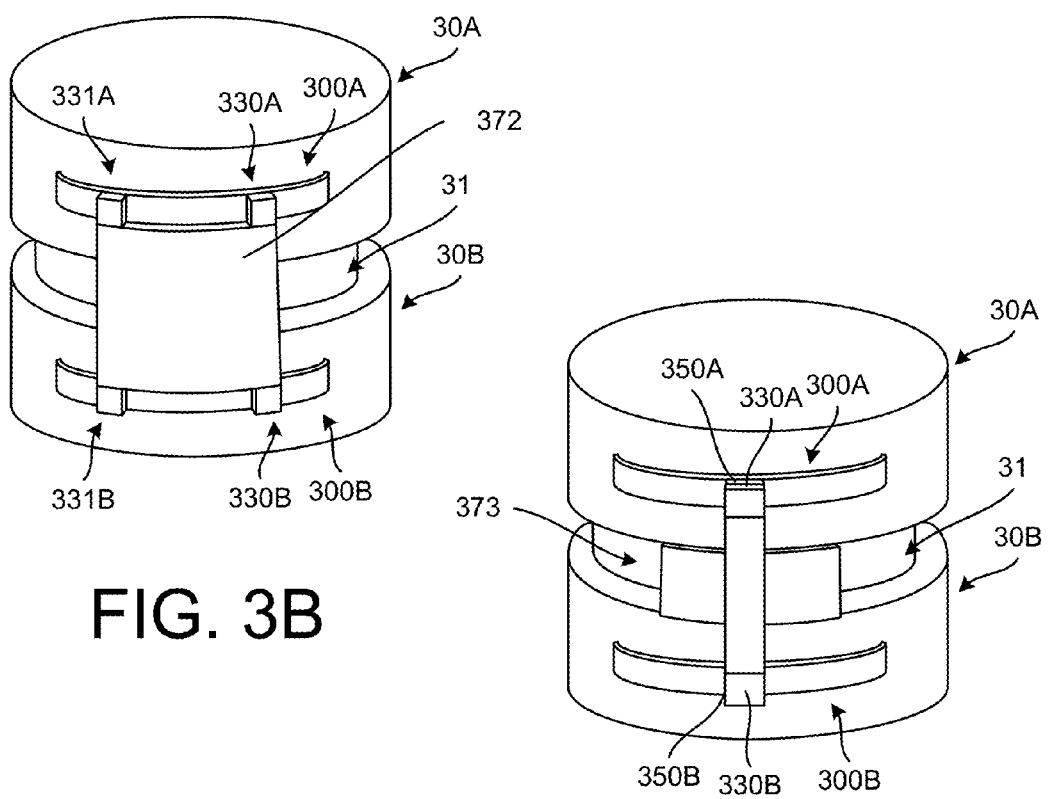
FIG. 3B
FIG. 3C

COMPLIANT VERTEBRAL ATTACHMENT DEVICE

RELATED APPLICATION

This application claims priority to and the benefit of U.S. Provisional Patent Application No. 62/107,921, filed Jan. 26, 2015, entitled, "Compliant Vertebral Attachment Device," which is incorporated herein by reference in its entirety.

FIELD

This disclosure relates, generally, to a vertebral attachment device.

BACKGROUND

The complex and non-uniform shape of the spinal vertebrae makes attachment and fixation of medical devices extremely challenging. To date, virtually all in vivo attachment to vertebrae has been through fixation that is destructive to the vertebral bone and can fail, especially in the context of osteoporosis.

SUMMARY

In one aspect, a vertebral attachment device can include an attachment member having a curved shape defining a concave surface, a flex structure included in the attachment member, and an anchor member coupled to the attachment member and protruding from the concave surface.

BRIEF DESCRIPTION OF THE DRAWINGS

FIGS. 3A through 3C illustrate multiple vertebral attachment devices attached respectively to multiple vertebrae.

DETAILED DESCRIPTION

Figure 1A:
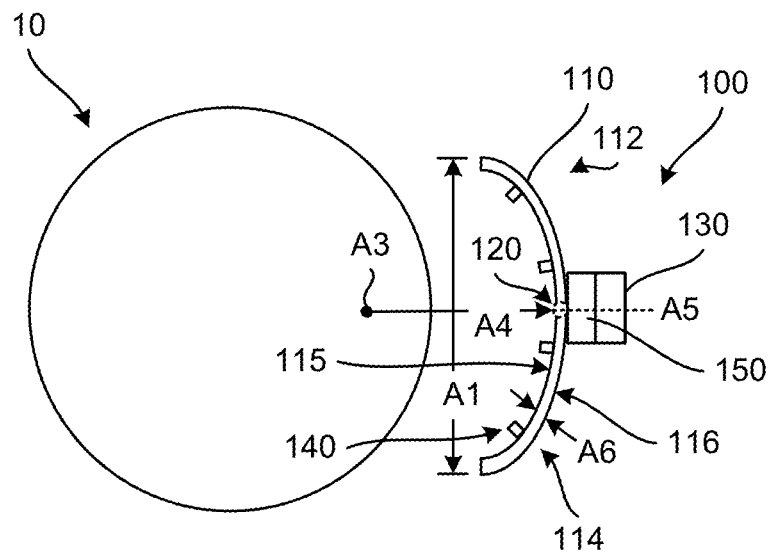
FIG. 1A is a diagram that illustrates a top view of a vertebral attachment device and a vertebrae, according to an implementation.

In this disclosure, implementations for a compliant mechanism vertebral attachment device that is non-destructive and/or conducive to future removal or surgical revision as needed is described. In some implementations, the device can be referred to as a compliant vertebral attachment device or as a vertebral attachment device.

Back pain can be one of the most common reasons for a physician visit with 80-85% of people suffering from some type of back pain at some point in their lifetime. As a result, significant attention has been devoted to the study of both the healthy and degenerated spine. Two main areas of spinal study are ex vivo testing of isolated spinal segments, as well as development of medical implants for treating spinal disorders. In both of these areas, a common challenge is that the complex and/or non-uniform shape of the vertebrae makes it difficult to attach devices to the spine. Currently, cementing materials are a common solution for ex vivo testing and screws can be used for in vivo instrumentation. Cementing materials can be highly exothermic, damaging soft tissue and destroying cellular function. In some instances, (especially when attached on the anterior aspect of the vertebrae), spinal screws can fail due to poor bone quality. Neither cementing materials, nor spinal screws are non-destructively revisable. Implementations of a vertebral attachment device that alleviates the earlier mentioned problems for both ex vivo and in vivo processes are described.

The irregular and/or complex shape of the spinal vertebrae can make it difficult for known devices to obtain a strong attachment. In addition, the bone quality in the spine may be poor and potentially exacerbate the problem. Another significant issue is that vertebral dimensions vary significantly based on vertebral level (e.g., cervical vs thoracic), as well as between individuals. The implementations described herein can be configured to securely and/or mechanically attach to vertebrae of different sizes and/or shapes. The implementations described herein can be configured to attach on an anterior side of a vertebra. The vertebral attachment device can be used to attach spinal treatment hardware (for example, fusion rods, dynamic stabilization devices, mechanical testing hardware, and/or so forth) to the spine. This could be for clinical treatment (e.g., spinal surgery), and/or for ex vivo mechanical testing (e.g., biomechanical testing).

A vertebral attachment device can be configured to be attached (e.g., coupled, clamped, coupled securely) to, for example, an anterior cortical shell of a vertebra. In some implementations, the vertebral attachment device can be configured to be attached to, for example, to a vertebra facilitating attachment of fusion or non-fusion spinal instrumentation. In some implementations, the vertebral attachment device can be used for, for example, in vivo spinal instrumentation, as well as for ex vivo biomechanical testing of cadaveric spine specimens.

The implementations of the vertebral attachment device described herein can be less time-consuming to attach, reusable (for the case of ex vivo testing), easily revisable (for surgical applications), less destructive to existing hard and/or soft tissue, and/or so forth, than known devices. In some implementations, the vertebral attachment device can, for example, have anchor members that penetrate the anterior cortical bone and/or provide increased resistance to bending but still allow it to be removed without excessive damage to the spine. In some implementations, the anchor members can be relatively thin needle-like structures. This device can be configured to grip (e.g., securely grip) the outer vertebral cortical shell without adding the invasive penetration that is commonly seen in so many other medical devices.

Figure 1B:
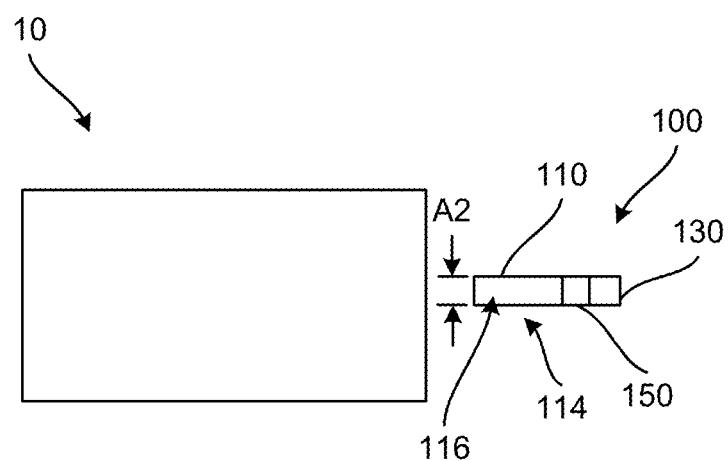
FIG. 1B is a diagram that illustrates a side view of the vertebral attachment device and the vertebrae shown in FIG. 1A, according to an implementation.

FIG. 1A is a diagram that illustrates a top view of a vertebral attachment device 100 and a vertebra 10, according to an implementation. FIG. 1B is a diagram that illustrates a side view of the vertebral attachment device 100 and the vertebra 10 shown in FIG. 1A, according to an implementation.

As shown in FIG. 1A (and FIG. 1B), the vertebral attachment device 100 includes an attachment member 110, a flex structure 120, a coupling mechanism 130, anchor members 140, and a locking mechanism 150. The vertebral attachment device 100 can be configured to be attached to (e.g., surgically attached to, coupled to) a vertebra 10 such that the anchor members 140 and/or the attachment member 110 are in contact with the vertebra 10. In some implementations, one or more of the anchor members 140 can be configured to have at least a portion disposed within the vertebra 10 when the vertebral attachment device 100 is attached to the vertebra 10.

The vertebral attachment device 100 (or a portion thereof) can be configured to move between a flexed configuration and a non-flexed configuration (e.g., a relaxed configuration). The vertebral attachment device 100 can be moved between the flexed configuration and the non-flexed configuration when being deployed for attachment to the vertebra 10. In some implementations, when the vertebral attachment device 100 is attached to the vertebra 10, the vertebral attachment device 100 can be in a configuration (e.g., a state) that is between the flexed configuration and the non-flexed configuration. In some implementations, when attached to the vertebra 10, the vertebral attachment device 100 can be in a partially flexed configuration (which is a configuration that is between the flexed configuration and the non-flexed configuration).

For example, the vertebral attachment device 100 can be in the configuration shown in FIG. 1A when in the non-flexed configuration. Specifically, the vertebral attachment device 100 can be biased to the non-flexed configuration, which can be a stable configuration. The vertebral attachment device 100 (or a portion thereof) can be moved to the flexed configuration in response to one or more forces being applied to one or more portions of the vertebral attachment device 100 such that vertebral attachment device 100 can be moved into position for attachment to the vertebra 10 (e.g., an anterior side of the vertebra 10). The vertebral attachment device 100 can be attached to the vertebra 10 as the one or more forces are removed from one or more portions of the vertebral attachment device 100. As (and after) the one or more forces are removed, the vertebral attachment device 100 can be attached to, and can maintain an attachment to, the vertebra 10. In some implementations, when attached to the vertebra 10 the vertebral attachment device 100 can be in a partially flexed configuration where the vertebral attachment device 130 exerts one or more forces on one or more portions of the vertebra 10. Accordingly, the vertebral attachment device 100, which can be biased to move toward the non-flex configuration, may maintain desirable contact with the vertebrate 10 because the vertebral attachment device 100 is in the partially flexed configuration.

In some implementations, after being attached to the vertebra 10, the vertebral attachment device 100 can be removed. Accordingly, the vertebral attachment device 100 can be removably coupled to the vertebra 10. In some implementations, the vertebral attachment device 100, after being attached to the vertebra 10, can be removed by applying one or more forces to one or more portions of the vertebral attachment device 100 such that the vertebral attachment device 100 can be removed from being attached to the vertebra 10. More details related to the components of the vertebral attachment device 100, moving of the vertebral attachment device 100 between configurations (e.g., the flexed configuration, the partially flexed configuration, the non-flexed configuration), attachment of the vertebral attachment device 100 to a vertebra (e.g., vertebra 10), and/or so forth are described below.

In comparison to known methods for vertebral fixation, the vertebral attachment device 100 can be less destructive (or non-destructive) during insertion. The implementations described herein can also provide an easier and/or less destructive removal process in the case of revision and/or re-use of the device. Use of the vertebral attachment device 100 described herein can also eliminate the potential for an (or any) exothermic reaction generated during polymerization of bonding agents, making the vertebral attachment device 100 more desirable for tissue. Overall, the implementations described herein can improve the vertebral attachment process for in vivo instrumentation and/or ex vivo biomechanical testing.

As shown in FIG. 1A, the attachment member 110 of the vertebral attachment device 100 has a curved shape (e.g., a curvature) defining both a concave surface 115 any convex surface 116. The convex surface 116 is on an opposite side of the attachment member 110 from the concave surface 115. In other words, the concave surface 115 is on a first side of the attachment member 110 and the convex surface 116 is on a second side of the attachment member 110.

The vertebral attachment device 100 is generally aligned within (or disposed within) a plane so that the attachment member 110 has a length A1 (as shown in the top view in FIG. 1A) that is greater than a width A2 of the attachment member 110 (as shown in the side view in FIG. 1B). In some implementations, a ratio of the length A1 to the width A2 can be 10:1 or greater (e.g., 15:1, 20:1, 30:1). In some implementations, the ratio of the length A1 to the width A2 can be less than 10:1 (e.g., 5:1, 2:1). In some implementations, the length A1 can be approximately between 20 and 50 millimeters. In some implementations, the width A2 can be approximately between 1 and 20 millimeters.

As shown in FIG. 1A, the attachment member 110 of the vertebral attachment device 100 has a center of curvature A3 and a radius of curvature A4. In some implementations, the curvature of one or more portions (e.g., arm portion 112, arm portion 114) of the attachment member 110 can be a circular curvature. In some implementations, the curvature of one or more portions (e.g., arm portion 112, arm portion 114) of the attachment member 110 can be a parabolic or non-parabolic curvature. In some implementations, the curvature of one or more portions (e.g., arm portion 112, arm portion 114) of the attachment member 110 can be an elliptical or non-elliptical curvature. In some implementations, the curvature of the attachment member 110 (or a portion thereof) can be non-circular (e.g., oval). In some implementations, the radius curvature A4 can be greater than the length A1 of the attachment member 110. In some implementations, the radius curvature A4 can be less than or equal to the length A1 of the attachment member 110. In this implementation, the radius of curvature A4 extends from the center of curvature A3 to a center (e.g., approximately a center) of the flex structure 120. In some implementations, the radius of curvature A4 can extend from the center of curvature A3 to a portion of the attachment member 110 (where the portion is separate from the flex structure 120). In some implementations, the radius of curvature A4 can be approximately between 20 and 100 millimeters.

In some implementations, the attachment member 110 (or a portion thereof) can be straight or linear (without a curvature). In some implementations, the attachment member 110 (or a portion thereof) can have multiple curved portions and/or straight/linear portions.

In some implementations, when moved between the flexed configuration and the non-flexed configuration (or partially flexed configuration), the radius of curvature A4 of the attachment member 110 can be changed. For example, when moved to the flexed configuration from the non-flexed configuration, the radius of curvature A4 of the attachment member 110 can be increased.

The curved shape (e.g., curvature) of the attachment member 110 of the vertebral attachment device 100 can enable the attachment member 110 to fit in a desirable fashion around the vertebra 10. In other words, the attachment member 110 can have a shape that can match the irregular curvature of the vertebra 10. In some implementations, the curved shape of the attachment member 110 can correspond with a curved shape of the vertebra 10. In some implementations, the curved shape of the attachment member 110 can be defined so that the attachment member 110 corresponds with a curvature of the vertebra 10 (of a specific patient). In some implementations, the curvature of the attachment member can be based on pre-operatively obtained medical imaging of the underlying bone contours such that it matches the contours and allows for maximum conformity of the clamp to the bone architecture. More details regarding dimensions of vertebral attachment devices will be described below in various parts of this detailed description.

The attachment member 110 has two arm portions—arm portion 112 and arm portion 114. In this implementation, each of the arm portions 112, 114 have a curved shape. The arm portion 112 has a curved shape but finds at least a portion of the concave surface 115 and a portion of the convex surface 116. Similarly, the arm portion 114 has at least a portion that defines the concave surface 115 and the convex surface 116.

As shown in FIG. 1A, the flex structure 120 of the attachment member 110 is disposed within a middle portion (e.g., central portion) of the attachment member 110. In this implementation, the flex structure 120 is disposed at a center of the attachment member 110. Specifically, a line along the radius of curvature A4 extends between the center of curvature A3 and the center of the flex structure 120 such that the line along the radius of curvature A4 bisects the length A1 of the attachment member 110. In some implementations, the flex structure 120 may not be disposed within a middle portion of the attachment member 110. In such implementations, the flex structure 120 can be offset in one direction or another along the attachment member 110. In such implementations, a line along the radius of curvature A4 can extend between the center of curvature A3 and the center of the flex structure 120 such that the line along the radius of curvature A4 does not bisect the length A1.

In this implementation, the arm portion 112 of the attachment member 110 extends away from the flex structure 120 in a first direction. The arm portion 114 of the attachment member 110 extends away from the flex structure 120 in a second direction substantially opposite the first direction. Accordingly, the attachment member 110 can be divided (e.g., conceptually divided) into the arm portions 112, 114 based on the position of the flex structure 120.

The flex structure 120 can be included in the attachment member 110 so that the arm portion 112 and/or the arm portion 114 can move (e.g., flex, bend). Accordingly, the attachment member 110 of the vertebral attachment device 100 can move between a flexed configuration and a non-flexed configuration using the flex structure 120. In some implementations, the flex structure 120 can function as a pivot point. In some implementations, when the attachment member 110 is moved between the flexed configuration and the non-flexed configuration, the vertebral attachment device 100 can be referred to as being moved between the flexed configuration and the non-flexed configuration.

In some implementations, the attachment member 110 can be biased to the curved shape as shown in FIGS. 1A and 1B. In other words, when in the non-flexed configuration, the attachment member 110 can be biased to the curved shape. During a medical procedure, the vertebral attachment device 100 can be moved between the flexed configuration and the non-flexed configuration as described above. More details related to movement between the flexed configuration in the non-flexed configuration are described below and in connection with at least FIGS. 2A through 2C.

In some implementations, the flex structure 120 can be, or can include, a recess, a notch (e.g., a V-shaped notch, a notch with a flat portion), and/or so forth in the attachment member 110. In such implementations, the flex structure 120 can define at least a portion of a discontinuity to the curved surface 115 of the attachment member 110. In some implementations, the flex structure 120 can extend across the entirety of, or less than the entirety of the width A2 of the attachment member 110. In some implementations, the flex structure 120 can extend across the entirety of, or less than the entirety of, a thickness A6 of the attachment member 110. In some implementations, the thickness A6 can be approximately between less than 0.5 and 6 millimeters.

In some implementations, the flex structure 120 can be, or can include, a portion of the attachment member 110 that is made of a different material than the attachment member 110. In some implementations, the flex structure 120 can be, or can include a portion of the attachment member 110 that has been formed (e.g., treated, modified) in a particular fashion so that the flex structure 110 can allow for movement of the attachment member 110 even though the flex structure 120 and the attachment member 110 are made of the same material. In some implementations, the flex structure 120 can include, or can be, a material that is softer than a material included in the remainder of the attachment member 110. In some implementations, the flex structure 120 can be defined or formed so that the vertebral attachment device 100 is a compliant mechanism. In some implementations, the flex structure 120 can include a hinge, a spring, and/or so forth.

In the implementation shown in FIG. 1A, the vertebral attachment device 100 is symmetric. Specifically, the attachment member 110 of the vertebral attachment device 100 is symmetric about the flex structure 120. Accordingly, the arm portion 112 has a length (e.g., a curved length, a linear length, a portion of the length A1 from an end of the arm portion 112 to approximately a line along the radius of curvature line A4) that is the same as a length (e.g., a curved length, a linear length, a portion of the length A1 from an end of the arm portion 114 to approximately a line along the radius of curvature line A4) of the arm portion 114. In other words, the arm portions 112, 114 have equal lengths in this implementation.

In some implementations, the vertebral attachment device 100 may be asymmetric (not shown in FIG. 1A). Specifically, in such implementations, the attachment member 110 of the vertebral attachment device 100 can be asymmetric about the flex structure 120. In such implementations, the arm portion 112 can have a length (as described above) that is different than a length of the arm portion 114. In such embodiments, the flex structure 120 may not be disposed within or along a middle portion or a center of the attachment member 110. In other words, the flex structure 120 can be offset from (e.g., not aligned along) a middle portion or a center of the attachment member 110. Said differently, the flex structure 120 can be offset from a middle portion or a center of the curved shape (or curvature) of the attachment member 110. In such implementations, the arm portions 112, 114 can have unequal lengths. Vertebral attachment device implementations that are asymmetrical can be beneficial for in vivo attachment. In some implementations, arm portions of different lengths (with one that is shorter than the other) can be desirable for a surgeon or researcher (e.g., during a medical procedure). These implementations can avoid interaction of the vertebral attachment device 100 with anatomical structures such as major blood vessels or organs located close to the device. More details related to asymmetric vertebral attachment devices are illustrated and described at least in connection with FIGS. 4A through 10C.

A vertebral attachment device having an asymmetric shape may allow for cleaning of the tissue around a vertebra on one side only. In a spinal procedure, particularly fusion procedures, an operator (e.g., a surgeon) may come into the spine at both the anterior and posterior sides. This type of surgery can be more invasive, more destructive, and potentially more dangerous. With the asymmetric configuration of the vertebral attachment device, the operator may be able to come in from a posterior side, and clear off a substantial portion of the tissue around the vertebral body. One way to completely clean off the vertebral body would be to make another incision from the posterior side closer to the other end of the vertebral body. This extra incision may be unnecessary with the asymmetrical configuration of the vertebral attachment device. Enough of the tissue can be cleared away from the vertebral body to allow for sufficient attachment of the vertebral attachment device. In some implementations, the asymmetric configuration of the vertebral attachment device can be used in ex vivo situations. In this case, the extra tissue can be cleared away prior to attachment.

Referring back to FIGS. 1A and 1B, the anchor members 140 protrude from the attachment member 110 of the vertebral attachment device 100. As shown in FIG. 1A (and not visible in FIG. 1B), the anchor members 140 are disposed on a side of the concave surface 115 of the vertebral attachment device 100. One or more of the anchor members 140 are configured to attach to (e.g., engage with, be coupled to, be embedded within) at least a portion of the vertebra 10 when the vertebral attachment device 100 is attached to the vertebra 10. In this implementation, only a few anchor members 140 are shown for description purposes. More anchor members, or less anchor members than shown in FIG. 1A can be included in a vertebral attachment device 100.

In some implementations, one or more of the anchor members 140 can be disposed on a same side of the vertebral attachment device 100 as the flex structure 120. Specifically, the anchor members 140 can protrude from the concave surface 115 and the flex structure 120 (or at least a portion thereof) can be disposed on a side of the attachment member 110 defining the concave surface 115.

In some implementations, the anchor members 140 of the vertebral attachment device 100 can, for example, penetrate the anterior cortical bone of the vertebra 10 and/or provide increased resistance of the attachment member 110 of the vertebral attachment device 100 to bending but can still allow the vertebral attachment device 100 to be removed without excessive damage the vertebra 10 (e.g., to the spine).

In some implementations, one or more of the anchor members 140 can be, or can have, an elongate structure. In some implementations, one or more of the anchor members 140 can have a cylindrical shape (e.g., a circular profile or cross-section) or a non-cylindrical shape (e.g., a square profile or cross-section, an oval profile or cross-section). In some implementations, one or more of the anchor members 140 can have a sharp end or pointed end. Accordingly, one or more of the anchor members 140 can have a relatively thin needle-like structure or can be a spike. In some implementations, one or more of the anchor members 140 can have a tapered shape (e.g., taper from a surface of the attachment member 110 toward an end of the anchor member).

In some implementations, one or more of the anchor members 140 can extend in a direction normal to (e.g., perpendicular to, substantially normal or perpendicular to) a surface (e.g., the concave surface 115) of the attachment member 110. In some implementations, one or more of the anchor members 140 can extend in a direction non-normal to (e.g., substantially non-normal to) a surface (e.g., the concave surface 115) of the attachment member 110. In some implementations, one or more of the anchor members 140 can extend linearly, or can be aligned along a longitudinal axis or line. In some implementations, one or more of the anchor members 140 can have a curved or nonlinear shape.

In some implementations, (e.g., where subsequent removal of the vertebral clamp is not anticipated), one or more of the anchor members 140 can have an end that can facilitate attachment to at least a portion of the vertebrate 10. For example, one or more of the anchor members 140 can have a protrusion, a barbed tip, a hook, an end ball, an arrowhead shape, and/or so forth.

In some implementations, the anchor members 140 can have the same, or similar lengths. In some implementations, the anchor members 140 can have different or non-uniform lengths. In some implementations, a first anchor member of the anchor members 140 can have a length that is different than a length of a second anchor member of the anchor members 140. In such implementations, the first anchor member can protrude from a surface (e.g., the concave surface 115) of the attachment member 110 to a different extent then the second anchor member protrudes from the surface of the attachment member 110. In some implementations, the anchor members 140 can have lengths between 0.1 and 10 millimeters. More details related to dimensions of anchor members are described below and at least in connection with FIGS. 5A and 5B.

The coupling mechanism 130 of the vertebral attachment device 100 shown in FIGS. 1A and 1B can be used to couple one or more peripheral devices (not shown) to the vertebral attachment device. For example, the coupling mechanism 130 can be used to attach one or more spinal treatment hardware devices such as a fusion rod, a dynamic stabilization device, a mechanical testing hardware device, a fusion cage, a plate, and/or so forth. In some implementations, the coupling mechanism 130 can include an opening, a hook, a latch, and/or so forth that can be used to couple one or more peripheral devices to the vertebral attachment device 100. Specific exemplar implementations of the coupling mechanism 130 are shown and described in connection with some of the figures below.

The locking mechanism 150 of the vertebral attachment device 100 can be used to attach the vertebral attachment device 100 to the vertebra 10. In some implementations, the locking mechanism 100 of the vertebral attachment device 100 can be used to securely (e.g., firmly) attach the vertebral attachment device to the vertebra 10. In some implementations, the locking mechanism 150 can be configured to exert a force against one or more portions of the vertebral attachment device 100 (e.g., one or more of arm portions 112, 114 of the attachment member) such that one or more portions of the vertebral attachment device 100 are securely attached to the vertebra 10. For example, after the vertebral attachment device 100 has been attached to the vertebra 10 and is in, for example, a partially flexed configuration, the locking mechanism 150 can be engaged to further maintain attachment of the vertebral attachment device 100 to the vertebra 10. Specifically, the locking mechanism 150 can be configured to exert a force against one or more portions of the vertebral attachment device 100 so that the one or more portions of vertebral attachment device 100 in turn exert a force on at least a portion of the vertebra 10.

In some implementations, the locking mechanism 150 can include one or more screws, compliant mechanisms (e.g., bi-stable compliant mechanisms), locking arms, springs, gears, press-fit components, a shim, locking teeth, and/or so forth. In some implementations, locking mechanism 150 can include a rotating component (e.g., a 90° rotating component) that causes the locking mechanism 150 to engage with one or more of the arm portions 112, 114. Specific exemplar implementations of the locking mechanism 150 are shown and described in connection with some of the figures below.

In some implementations, a peripheral device such as a plate (not shown in FIG. 1A or 1B) can be attached onto the anterior of the clamp with the coupling mechanism 130 and/or locking mechanism 150 that secures the vertebral attachment device 100 in the attached configuration until the lock is removed. In some implementations, various coupling mechanisms 130 and/or locking mechanisms 150 can be utilized. In some implementations, spinal instrumentation or testing hardware can also be attached via the peripheral device (e.g., integrated plate).

As shown in FIGS. 1A and 1B, the coupling mechanism 130, the locking mechanism 150 and the flex structure 120 are aligned along the line A5 (which bisects the attachment member 110 into arm portions 112, 114 having equal lengths). Accordingly, the coupling mechanism 130, locking mechanism 150, and the flex structure 120 are aligned with one another. In this implementation, line A5 is aligned with (and intersects) the radius of curvature A4, which intersects both the center of curvature A3 and the flex structure 120.

In some implementations, the flex structure 120 can be on a first side of the attachment member 110 and the coupling mechanism 130 and/or the locking mechanism 150 can be on an opposite side (e.g., directly on an opposite side) of the attachment member 110. In other words, the coupling mechanism 130 and/or locking mechanism 150 can be directly on an opposite side of the attachment member 110 from the flex structure 120.

In some implementations, the flex structure 120, the coupling mechanism 130, and/or locking mechanism 150 can be oriented with respect to one another in a configuration that is different than is shown in FIGS. 1A and 1B. For example, in some implementations, the flex structure 120 may not be aligned along line A5 with both the coupling mechanism 130 and/or the locking mechanism 150 but instead can be on a different portion of the attachment member 110. In such implementations, the flex structure 120 may not be directly on an opposite side of the coupling mechanism 130 and/or locking mechanism 150. As another example, the coupling mechanism 130 may not be aligned along A5 along with locking mechanism 150 and/or the flex structure 120. As yet another example, the coupling mechanism 130, the locking mechanism 150, and/or the flex structure 120 may not be aligned along a line that bisects the attachment member 110 into arm portions 112, 114 having equal lengths. As yet another example, the coupling mechanism 130, the locking mechanism 150, and/or the flex structure 120 may be aligned along a line, but the line may not bisect the attachment member 110 into arm portions 112, 114 having equal lengths.

In this implementation, the locking mechanism 150 is disposed between the flex structure 120 and the coupling mechanism 130. Also, the coupling mechanism 130 is directly coupled to locking mechanism 150, which is directly coupled to the convex surface 116 of the attachment member 110.

In some implementations, the locking mechanism 150 may not be disposed between the flex structure 120 (or attachment member 110) and the coupling mechanism 130. For example, in some implementations, the coupling mechanism 130 can be disposed between the locking mechanism 150 and the flex structure 120 (or attachment member 110). As another example, the locking mechanism 150 can be coupled to a different portion of the attachment member 110 than shown in FIGS. 1A and 1B. In such implementations, the coupling mechanism 130 may be attached directly to (e.g., directly to the convex surface 116 of) the attachment member 110. As yet another example, locking mechanism 150 and the coupling mechanism 130 can be directly coupled to the attachment member 110. In such implementations, the locking mechanism 150 or the coupling mechanism 130 can be directly on an opposite side of the attachment number 110 from the flex structure 120 or may not be directly on an opposite side of the attachment member 110 from the flex structure 120.

Although not shown in FIG. 1A or 1B, the vertebral attachment device 100 can include more than one coupling mechanism 130. Also, in some implementations, the vertebral attachment device 100 can include more than one locking mechanism 150. Also, in some implementations, the vertebral attachment device 100 can include more than one flex structure 120. In such implementations, the attachment member 110 of the vertebral attachment device 100 can include more than two arm portions.

Although the vertebral attachment device 100 includes an attachment member 110 that has two arm portions of this implementation. In some implementations, the attachment member 110 can have a single arm portion. In such implementations, the vertebral attachment device 100 can exclude the flex structure 120. In such implementations, the vertebral attachment device 100 can include one or more locking mechanisms and or coupling mechanisms.

In some implementations, the attachment member 110 can have more than two arm portions. In such implementations, one or more arm portions can extend and/or curve in directions that are inside or outside of the planes of the figures shown in FIGS. 1A and 1B. More details related to a vertebral attachment device including more than two arm portions are shown and described below and in connection with at least FIGS. 12, 13, and 14.

In some implementations, one or more arm portions (e.g., arm portions 112, 114) can extend and/or curve in directions that are inside or outside of the plane of the figures shown in FIGS. 1A and 1B. In some implementations, one or more arm portions can, for example, curve in more than one direction. An example of such an implementation is illustrated and described in connection with FIGS. 11A and 11B.

Figure 11A:
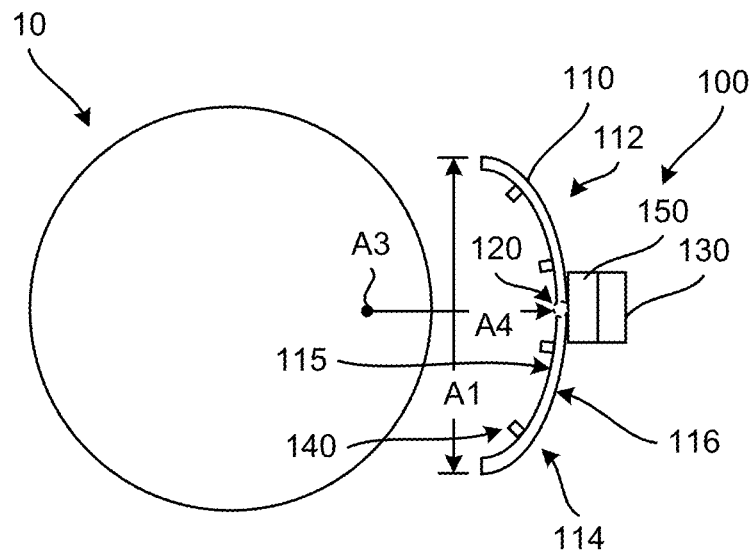
FIGS. 11A and 11B are variations of the vertebral attachment device shown in FIGS. 1A and 1B that includes arm portions that extend in multiple directions.
Figure 11B:
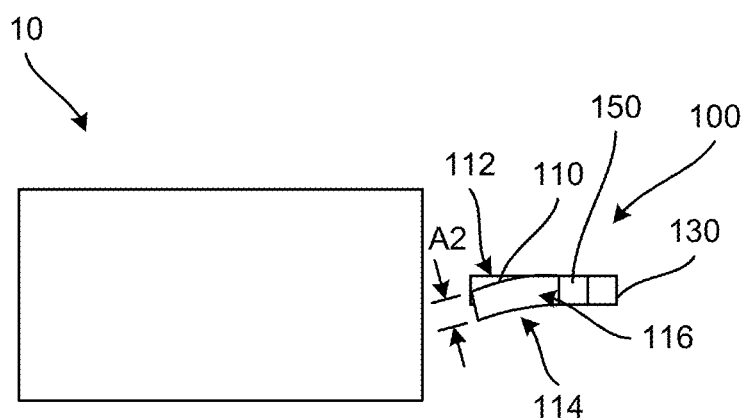

FIGS. 11A and 11B are variations of the vertebral attachment device 100 that includes arm portions that extend in multiple directions that are inside or outside of the plane figures shown in FIGS. 1A and 1B. The features shown in FIGS. 11A and 11B can include any of the features described in connection with FIGS. 1A and 1B. As shown in FIG. 11B the arm portion 114 curves in a downward direction. Accordingly, the arm portion 114 curves in two directions—curves in a first direction within a first plane (when projected two-dimensionally) as shown in the top view in FIG. 11A and curves in a second direction within a second plane (when projected two-dimensionally) as shown in the side view in FIG. 11B. In this implementation, arm portion 112 does not curve in two directions. In some implementations, arm portion 112 can be configured to curve in two directions similar to arm portion 114, or in a directions different than arm portion 114.

The vertebral attachment device 100 can be made of, or can include, one or more materials including polymers, ceramics, and/or metals (e.g., stainless steel, titanium, aluminum, etc.). For certain applications, the vertebral attachment device 100 can be made of a bioabsorbable polymer and/or bioabsorbable ceramic. In some implementations, the vertebral attachment device 100 can be made of a shape memory alloy such as nitinol.

In some implementations, the vertebral attachment device 100 (or a portion thereof) can be monolithically formed (e.g., formed using a stamping process, formed using a laser cutting process, formed using a 3-D printing process). In other words, the vertebral attachment device 100 can be formed monolithically from one or more of the materials described above. For example, the attachment member 110, the flex structure 120, the coupling mechanism 130, the anchor members 140, and the locking mechanism 150 of the vertebral attachment device 100 can be monolithically formed. In such implementations, one or more components such as a screw, a pin, and/or so forth may not be monolithically formed (e.g., may be excluded from the monolithic formation) as part of the vertebral attachment device 100.

In some implementations, one or more portions of the vertebral attachment device 100 can be separately formed and attached via one or more mechanisms (e.g., a weld, an adhesive, a screw, a snap fit, and/or so forth) and/or methods. For example, the attachment member 110, the flex structure 120, and the anchor members 140 can be monolithically formed. The coupling mechanism 130 and/or locking mechanism 150 can be separately formed and attached to these other components via, for example, an adhesive or a weld.

Although not explicitly shown or labeled, many, or all, of the features described in connection with FIGS. 1A and 1B can be incorporated into many of the implementations described below. Accordingly, many of the implementations described below are implementations, or variations, of the vertebral attachment device 100 shown and described in connection with FIGS. 1A and 1B.

Figure 2A:
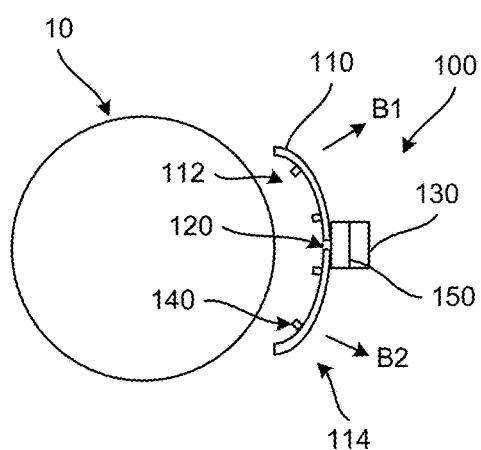
FIGS. 2A through 2C illustrate a process for attaching the vertebral attachment device to the vertebrae shown in FIGS. 1A and 1B.
Figure 2B:
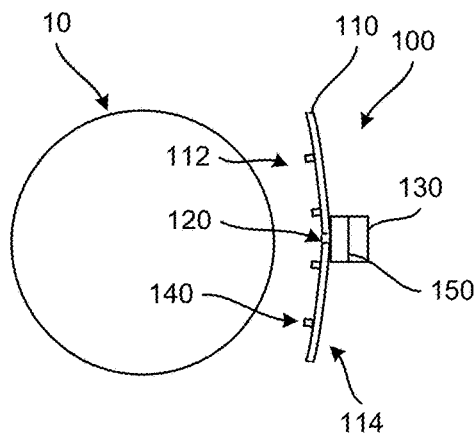
Figure 2C:
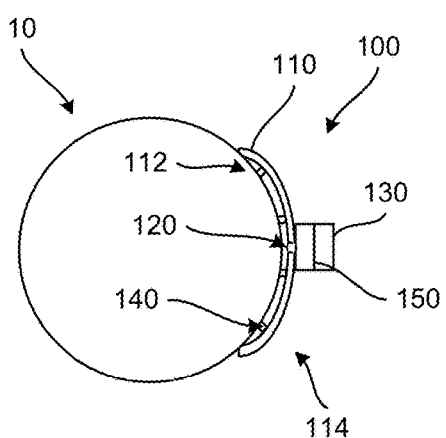

FIGS. 2A through 2C illustrate a process for attaching the vertebral attachment device 100 shown in FIGS. 1A and 1B to the vertebra 10. As shown in FIG. 2A, the vertebral attachment device 100 can be in a non-flexed configuration. The vertebral attachment device 100 can be biased to the non-flexed configuration, which can be a stable or rest configuration.

The vertebral attachment device 100 (or a portion thereof) can be moved to the flexed configuration in response to force B1 being applied to the arm portion 112 and to force B2 being applied to the arm portion 114. The force B1 can generally be applied in a direction opposite the direction in which at least some of the anchor members are protruding from the concave surface of the attachment member 110. Similarly, force B2 can generally be applied in a direction opposite direction which at least some of the anchor members are protruding from the concave surface of the attachment member 110. In other words, one of the anchor members 140 can protrude from the concave surface in a first direction, and the arm portion 112 of the attachment member 110 can be moved in a second direction substantially opposite the first direction. Although not shown, in some implementations, the forces B1, B2 can be applied using a tool during, for example, a medical procedure or during research. In some implementations, movement between the flex configuration and the non-flexed configuration can be enabled by the flex structure 120.

The vertebral attachment device 100 can be attached to the vertebra 10 as the forces B1, B2 are removed from the arm portions 112, 114 the vertebral attachment device 100. In some implementations, the forces B1, B2 can be removed (at least partially removed) after the vertebral attachment device 100 has come in contact with the vertebra 10, or can be removed (at least partially removed, before the vertebral attachment device 100 has come in contact vertebra 10. In some implementations, the attachment to the vertebra 10 can be performed on an anterior side of the vertebra 10. In some implementations, attachment to the vertebra 10 can be performed laparoscopically.

As shown in FIG. 2C, vertebral attachment device 100 is attached to the vertebra 10. In some implementations, the vertebral attachment device 100 can be in the non-flexed configuration when attached to the vertebra 10. In some implementations, the vertebral attachment device 100 can be in a partially flexed configuration when attached to the vertebra 10. The partially flexed configuration can be a configuration that is between the flexed configuration and the non-flexed configuration. In such implementations, one or more of the arm portions 112, 114 can exert at least a portion of a force on the vertebra 10. Accordingly, the anchor members 140 can exert a force on the vertebra 10. Accordingly, the vertebral attachment device 100, which can be biased to move toward the non-flex configuration, may maintain desirable contact with the vertebrate 10 because the vertebral attachment device 100 is in the partially flexed configuration.

In some implementations, after the vertebral attachment device 100 is attached to the vertebra 10, the locking mechanism 150 can be engaged. Also, after or before the vertebral attachment device 100 is attached to the vertebra 10, or more peripheral devices (not shown) can be coupled to the coupling mechanism 130.

In some implementations, after being attached to the vertebra 10, the vertebral attachment device 100 can be removed. Accordingly, the vertebral attachment device 100 can be removably coupled to the vertebra 10. In some implementations, the vertebral attachment device 100, after being attached the vertebra 10, can be removed by applying one or more forces (e.g., force B1, B2) to one or more of the arm portions 112, 114.

FIGS. 3A through 3B illustrate multiple vertebral attachment devices 300A, 300B attached respectively to multiple vertebrae 30A, 30B. In these implementations, various types of peripheral devices are coupled to the vertebral attachment devices 300 A, 300 B.

In the implementation shown in FIG. 3A, a peripheral device 371 is coupled between the coupling mechanism 330A of the vertebral attachment device 300A and the coupling mechanism 330B of the vertebral attachment device 300B. In some implementations, the peripheral device 371 can be, for example, a fusion rod. For example, the peripheral device 371 can have, for example, a cylindrical shape or profile. In some implementations, the peripheral device 371 can have, for example, a non-cylindrical shape or cross-section (e.g., a square cross-section, a tapered cross-section, an oval cross section). The peripheral device 371 can have an end disposed, for example, within an opening defined within the coupling mechanism 330A. An end of the peripheral device 371 can be coupled to the coupling mechanism 330A and/or 330B by, for example, a screw, a latch, and/or so forth.

In the implementation shown in FIG. 3B, a peripheral device 372 is coupled between the coupling mechanisms 330A, 331A of the vertebral attachment device 300A and the coupling mechanism 332A, 332B of the vertebral attachment device 300B. In some implementations, the peripheral device 371 can be, for example, a plate. In some implementations, the plate can have, for example, a rectangular shape or profile (when projected in 2 dimensions). In some implementations, the plate can have, for example, a curved shape. The peripheral device 372 can be coupled (e.g., maintained within) the coupling mechanism 330A by, for example, a screw, a latch, and/or so forth.

Although not shown, in some implementations, multiple peripheral devices can be coupled to the multiple coupling mechanisms 330A, 330B, 331A, 331B. For example, a first peripheral device (e.g., a first fusion rod) can be coupled between 330A, 330B, and a second peripheral device (e.g., a second fusion rod) can be coupled between 331A, 331B.

In the implementation shown in FIG. 3C, a peripheral device 373 is coupled between the coupling mechanism 330A of the vertebral attachment device 300A and the coupling mechanism 330B of the vertebral attachment device 300B. In some implementations, the peripheral device 373 can be, for example, a fusion cage that can be coupled via a rod or some other component. The peripheral device 373 (e.g., fusion cage) can have at least a portion disposed between the vertebrae 30A, 30B. For example, the peripheral device 373 can have an end disposed, for example, within an opening defined within the coupling mechanism 330A. An end of the peripheral device 373 can be coupled to the coupling mechanism 330A and/or 330B by, for example, a screw, a latch, and/or so forth.

FIGS. 4A through 4D are diagrams that illustrate a vertebral attachment device 400 that has arm portions 412, 414 of unequal length. The vertebral attachment device 400 can be a variation of the vertebral attachment device 100 shown in FIGS. 1A and 1B.

The vertebral attachment device 400 has an attachment member 410 including a flex structure 420 and having a convex surface 416 and a concave surface 415. The attachment member 410 includes anchor members 440 protruding from the concave surface 415. As shown, anchor members are excluded from the flex structure 420. The attachment member 410 includes a locking mechanism 450 and a coupling mechanism 430.

In this implementation, the locking mechanism 450 and the coupling mechanism 430 are aligned with the flex structure 420 and/or offset (e.g., not aligned along) from a line C1 bisecting the attachment member 410. Accordingly, the arm portion 412 is shorter than the arm portion 414.

In this implementation, each of the arm portions 412, 414 has a rounded end that is, or includes, a protrusion. These rounded ends can be defined so that during a procedure, the ends of the arm portions 412, 414 may not cause undesirable damage. In some implementations, the ends of the arm portions 412, 414 can have a different shape such as a different curved shape, or a non-curved shape. In some implementations, the rounded ends may be configured such that they align with the contours of the underlying vertebra and increase the strength of the attachment to the vertebra.

Figure 4A:
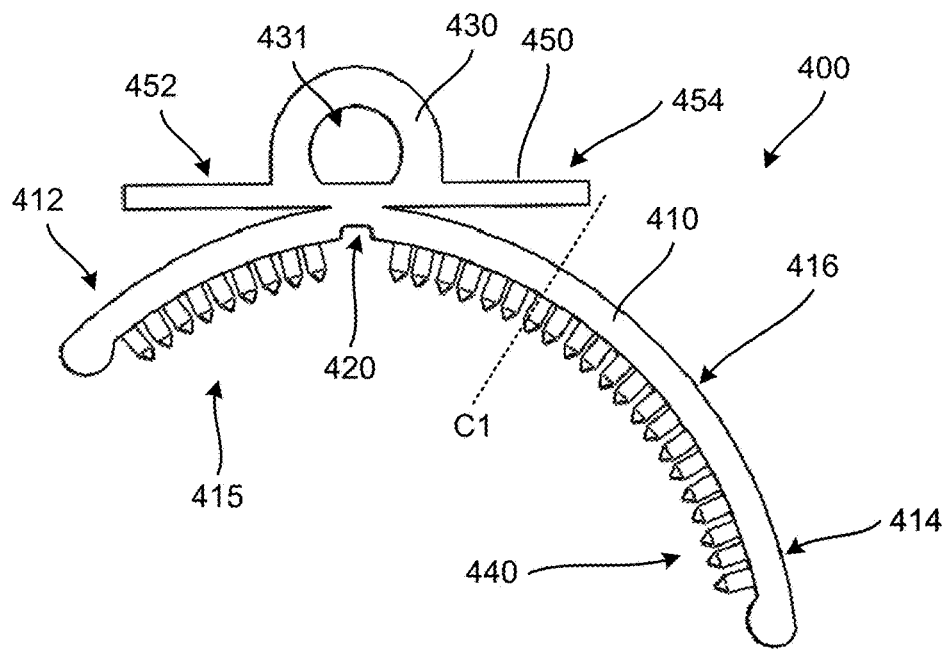
FIGS. 4A through 4D are diagrams that illustrate another vertebral attachment device.

As shown in FIG. 4A, the coupling mechanism 430 has, or defines, an opening 431 there. In some implementations, a peripheral device can be coupled to, or can be disposed within, the opening 431. In this implementation, the opening 431 has a D-shaped profile or cross-section (which can substantially prevent axial rotation of a peripheral device disposed therein). In some implementations, the opening 431 can have a different profile or cross-sectional shape (e.g., an oval shape, a square shape, a star shape, etc.). In some implementations, the coupling mechanism can include a recess or notch for a peripheral device that is not an opening all the way through. In some implementations, coupling between the vertebral attachment device 400 and the peripheral device can be accomplished using attachment screws.

Figure 4B:
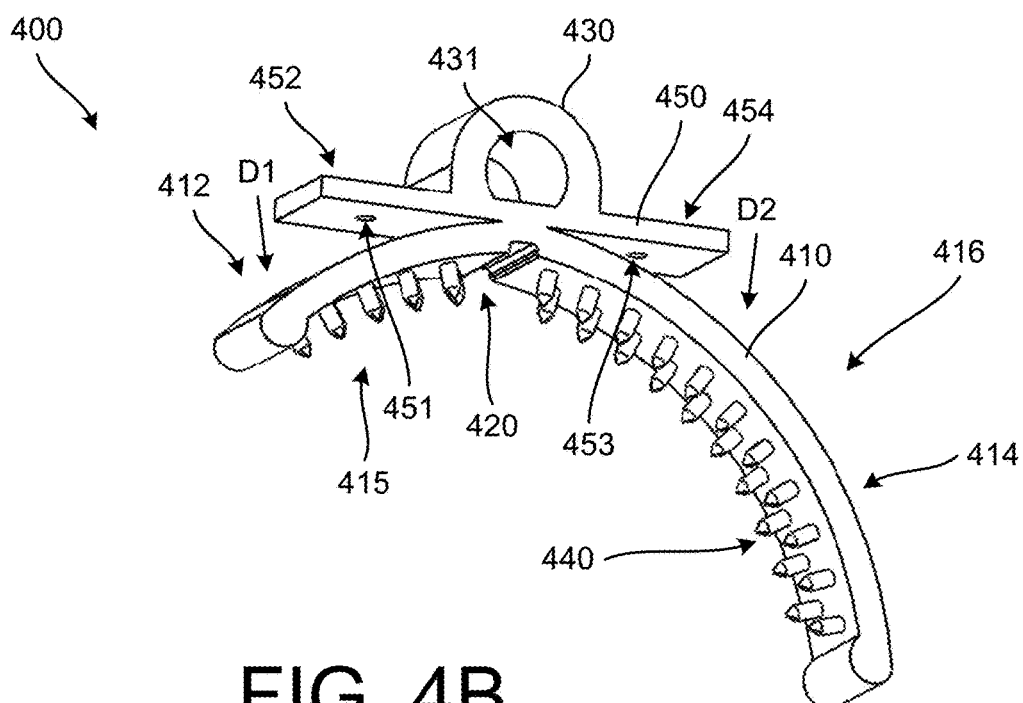

FIG. 4B is a perspective view of the vertebral attachment device 400. As shown in FIG. 4B, the locking mechanism 450 has locking arms 452, 454. In some implementations, the locking mechanism 450 can have less than two locking arms, or more than two locking arms. In this implementation, the locking arms 452, 454 have equal lengths. In some implementations, the locking arms 452, 454 can have different lengths. In some implementations, the locking arms 452, 454 can have different widths that can be different than the widths of the arm portions 412, 414. In some implementations, the locking arms 452, 454 can have a curved shape that can be different than curved shapes of the arm portions 412, 414. One or more spaces or gaps can be disposed between at least a portion of one or more of the locking arms 452, 454 and at least a portion of one or more of the arm portions 412, 414.

In this perspective view, openings 451 and 453 can be seen. Through these openings 451, 453 a locking member (not shown) such as a screw, or a pin can be disposed and used to apply forces D1, D2 against the arm portions 412, 414. The directions of the forces D1, D2 can be opposite (e.g., substantially opposite) a direction of forces used to change the vertebral attachment device 400 from a non-flexed configuration to a flexed configuration. In some implementations, the locking mechanism 450 can be engaged when the vertebral attachment device 400 is in a partially flexed configuration.

Figure 4C:
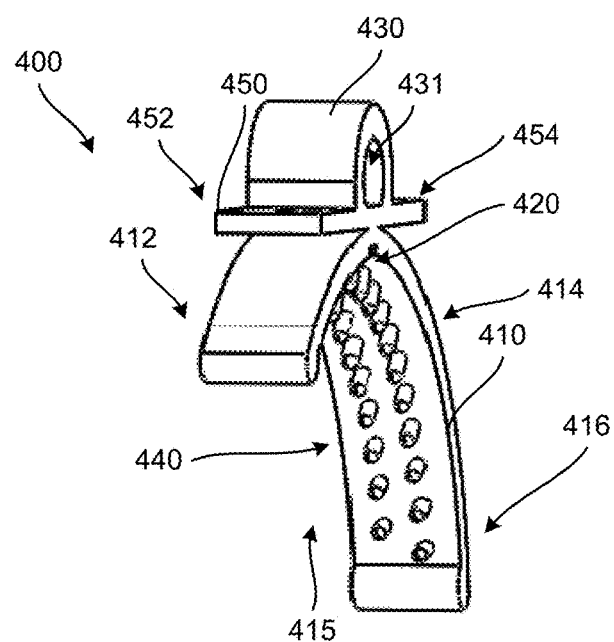
Figure 4D:
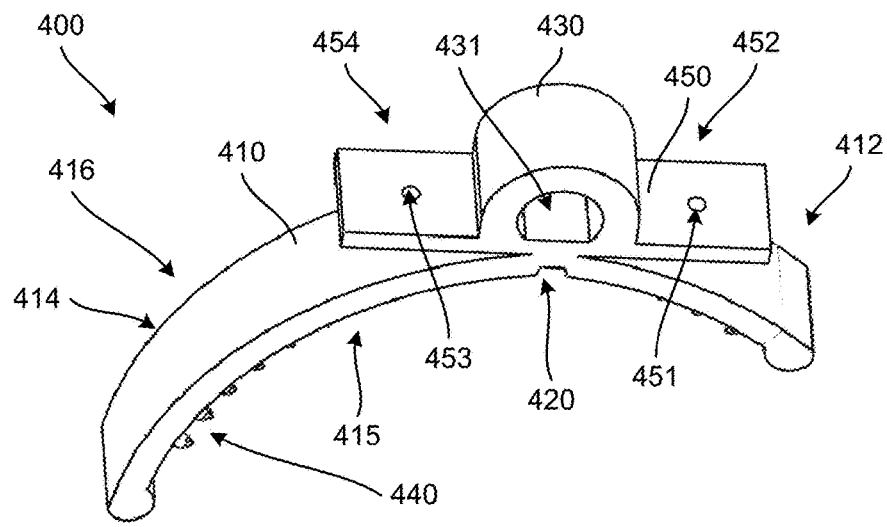

FIGS. 4C and 4D are additional perspective views of the vertebral attachment device 400.

Figure 5A:
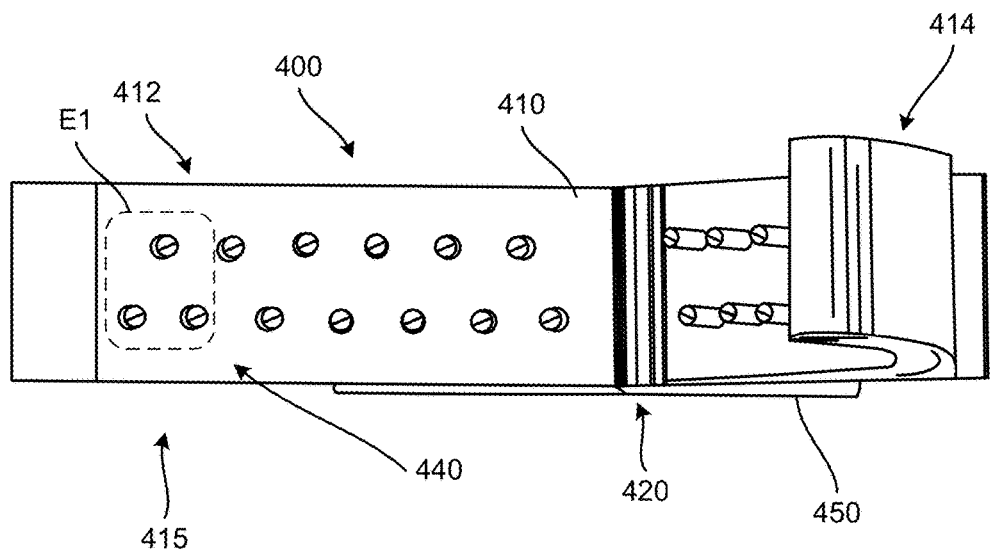
FIGS. 5A and 5B are diagrams that illustrate the anchor members of the vertebral attachment device shown in FIGS. 4A through 4D.
Figure 5B:
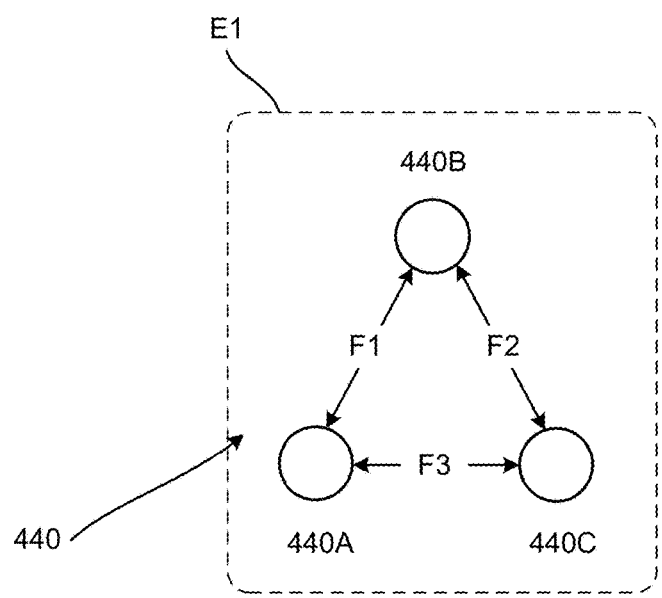

FIGS. 5A and 5B are diagrams that illustrate the anchor members 440 of the vertebral attachment device 400 shown in FIGS. 4A through 4D. As shown in FIGS. 5A and 5B, the anchor members 440 in this implementation are generally arranged in a triangular pattern. The anchor members 440 in this implementation are generally aligned in two rows that are linearly arranged. Also, each of the anchor members 440 has a same diameter or cross-sectional profile.

In some implementations, the anchor members 440 (or a portion thereof) can be arranged in a different pattern (e.g., a square pattern, a rectangular pattern, a pentagonal pattern, a hexagonal pattern, a random pattern). In some implementations, the anchor members 440 (or a portion thereof) can be arranged in more than two rows, or less than two rows that may or may not be linearly arranged. In some implementations, one or more of the anchor members 440 (or portion thereof) can have a different diameter and/or cross-sectional profile (e.g., square cross-sectional profile, etc.) than other of the anchor members 440.

FIG. 5B illustrates a zoomed in portion E1 of a few of the anchor members 440. FIG. 5B illustrates anchor members 440A, 440 B, and 440 C. In this implementation, the anchor members 440A through 440C are arranged equidistant apart. Specifically, a distance F1 between for 440A and 440B is the same as a distance F2 between 440C and 440B and is the same as a distance F3 between 440A and 440C.

In this implementation, the distances F1, F2, and F3 are each 3 times a diameter of any of the individual anchor members 440A through 440C. As a specific example, the distance F1 between anchor members 440A and 440B can be three times a diameter of the anchor member for 440A. The distances between the anchor members 440A through 440C can be measured as the distance between the nearest neighbor anchor member without intervening anchor members. In some implementations, the distances F1 through F3 can be between a fraction of a millimeter and a few centimeters.

In some implementations, the distances F1 through F3 can be at least (e.g., a minimum of) 3 times the diameter of the individual anchor members 440A through 440C so that when the anchor members 440A through 440C are engaged with a vertebra (not shown), the pressure exerted by the anchor members 440A through 440C may not damage the vertebra in an undesirable fashion. In some implementations, one or more of the distances F1 through F3 can be at least 3 times (e.g., 4 times, 5 times) the diameter of the anchor members 440A through 440C, equal to 3 times the diameter of the anchor members 440A through 440C, and/or less than 3 times (e.g., 2 times, 1.5 times, 1 time) the diameter of the anchor members 440A through 440C.

In some implementations, not all anchor members 440 may be engaged with the vertebra when the vertebral attachment device 400 is attached to vertebra. In some implementations, the vertebral attachment device 400 can be configured so that less than 50% of the anchor members 440 may be engaged with the vertebra. In some implementations, the vertebral attachment device 400 can be configured so that approximately, or more than 50% of the anchor members 440 may be engaged with the vertebra.

Figure 6A:
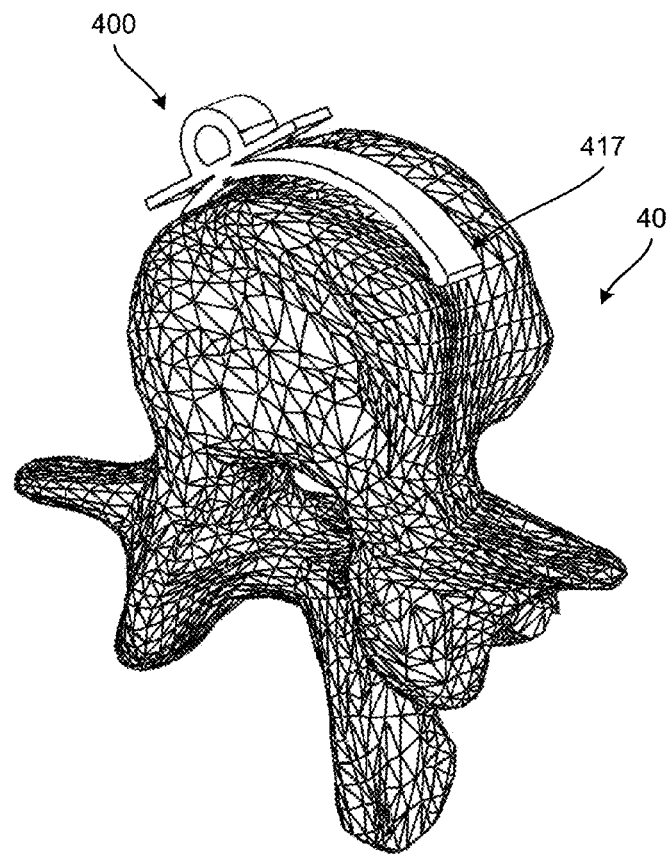
FIGS. 6A through 6C are various views that illustrate the vertebral attachment device shown in FIGS. 4A through 5B coupled to a vertebrae.
Figure 6B:
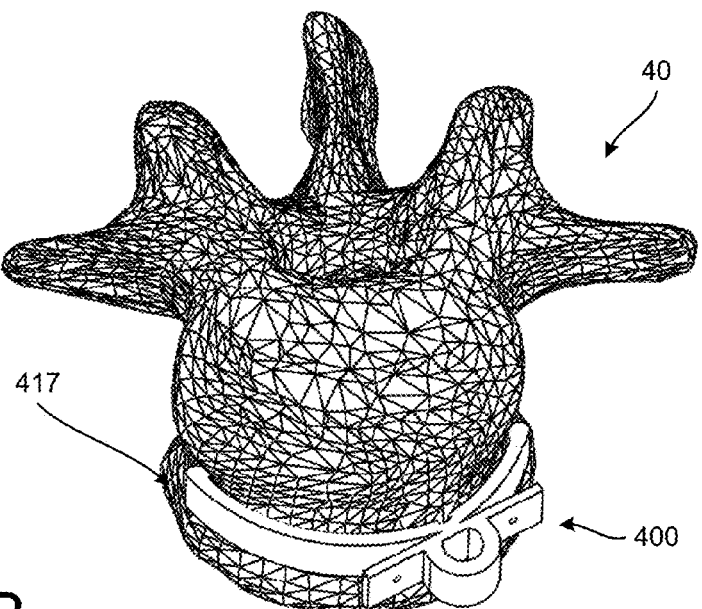
Figure 6C:
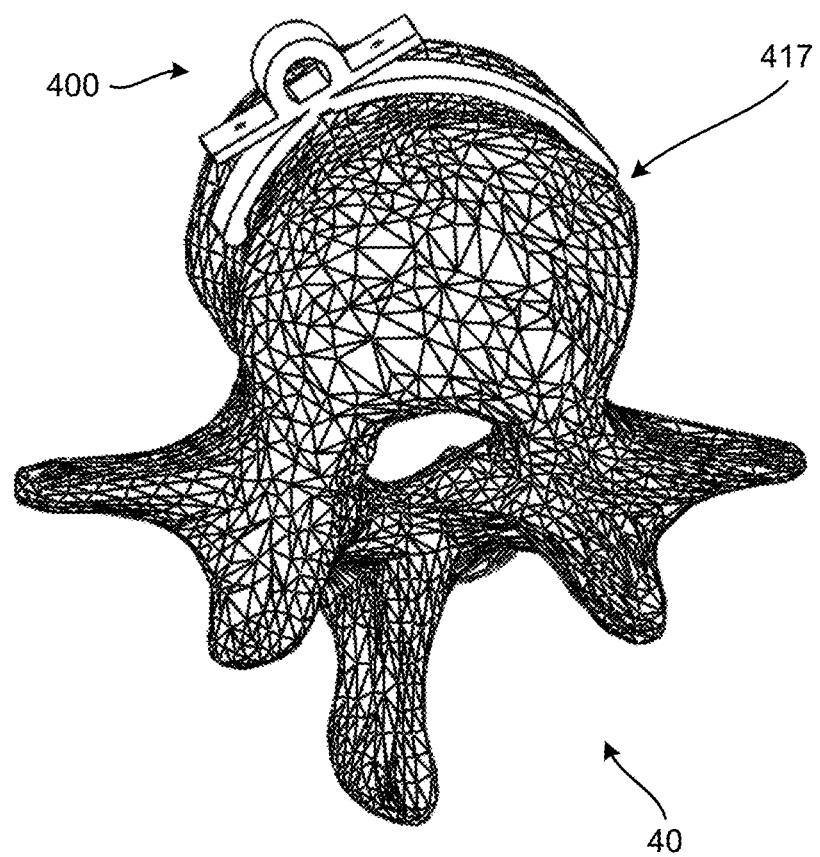

FIGS. 6A through 6C are various perspective views that illustrate the vertebral attachment device 400 shown in FIGS. 4A through 5B coupled to a vertebra 40. In this implementation, an end portion 417 of at least one of the arm portions is configured to have at least a portion disposed within a vertebral fovea of the vertebra 40. In some implementations, the end portion 417 can include a protrusion, a rounded portion, and/or so forth that can be disposed within the vertebral fovea.

Figure 7:
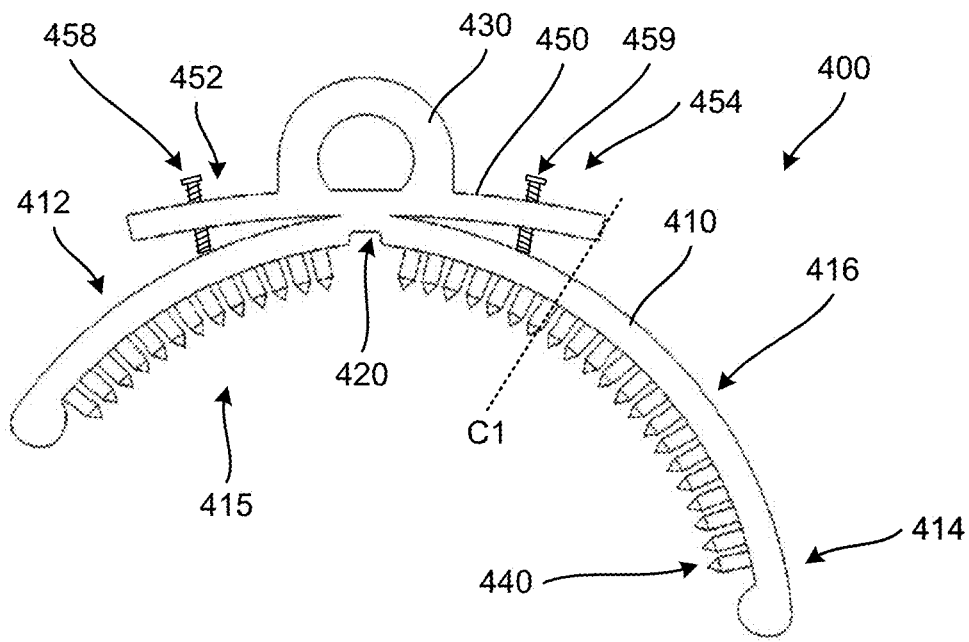
FIG. 7 is a diagram that illustrates a variation of the vertebral attachment device shown in FIGS. 4A through 6C.

FIG. 7 is a diagram that illustrates a variation of the vertebral attachment device 400 shown in FIGS. 4A through 6C. As shown in FIG. 7, the vertebral attachment device 400 has curved locking arms 452, 454. In this implementation, a radius of curvature of the locking arms 452, 454 can be different than a radius of curvature of the arm portions 412, 414. Because the locking arms 452, 454 are curved, screws 458, 459 that are included in the locking mechanism 450 may engage in a more desirable fashion with the arm portions 412, 414. Specifically, a bottom portion of the screws 458, 459 may be engaged at a relatively normal or perpendicular angle with respect to the concave surface 416 of the attachment member 410. As described above, in some implementations, locking mechanism 450 can have less than two locking arms. In some implementations, openings through which the screws 458, 459 are disposed can be between a fraction of a millimeter and a few millimeters.

In some implementations, the radius of curvature of one or more of the locking arms 452, 454 can be less than half of the radius of curvature of one or more of the arm portions 412, 414. In some implementations, the radius of curvature of one or more of the locking arms 452, 454 can be greater than or less than half of the radius of curvature of one or more of the arm portions 412, 414.

In some implementations, a thickness (not labeled) of one or more of the locking arms 452, 454 can be less than a thickness (not labeled) of one or more of the arm portions 412, 414. In some implementations, a thickness of one or more of the locking arms 452, 454 can be greater than or equal to a thickness of one or more of the arm portions 412, 414.

In some implementations, a linear length (and/or curved length) (not labeled) of one or more of the locking arms 452, 454 can be less than a linear length (and/or curved length) (not labeled) of one or more of the arm portions 412, 414. In some implementations, the linear length (and/or curved length) of one or more of the locking arms 452, 454 can be greater than or equal to the linear length (and/or curved length) of one or more of the arm portions 412, 414.

Figure 8:
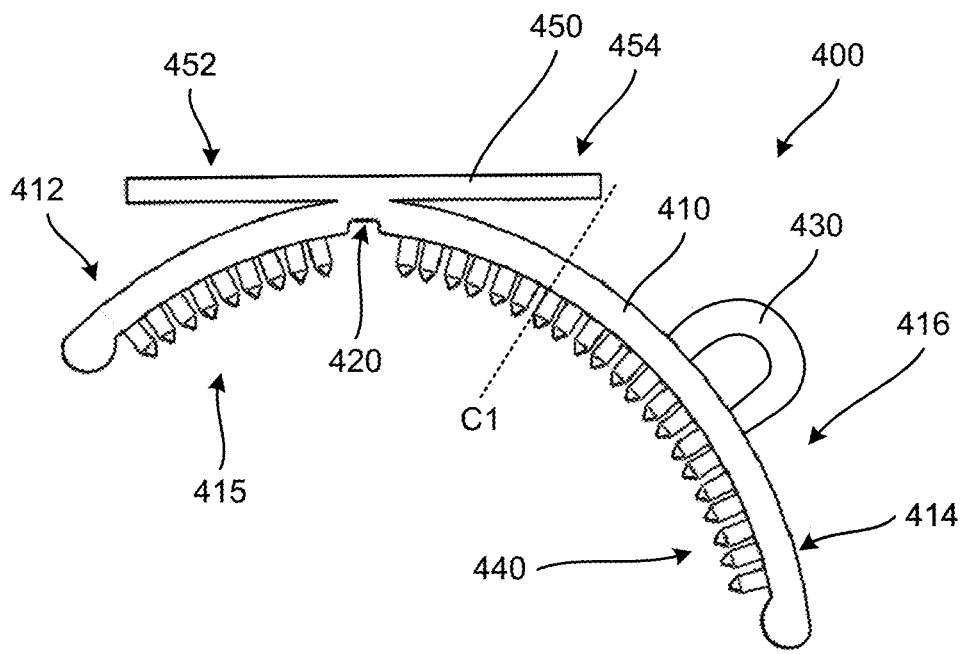
FIG. 8 is a diagram that illustrates another variation of the vertebral attachment device shown in FIGS. 4A through 7.
Figure 9A:
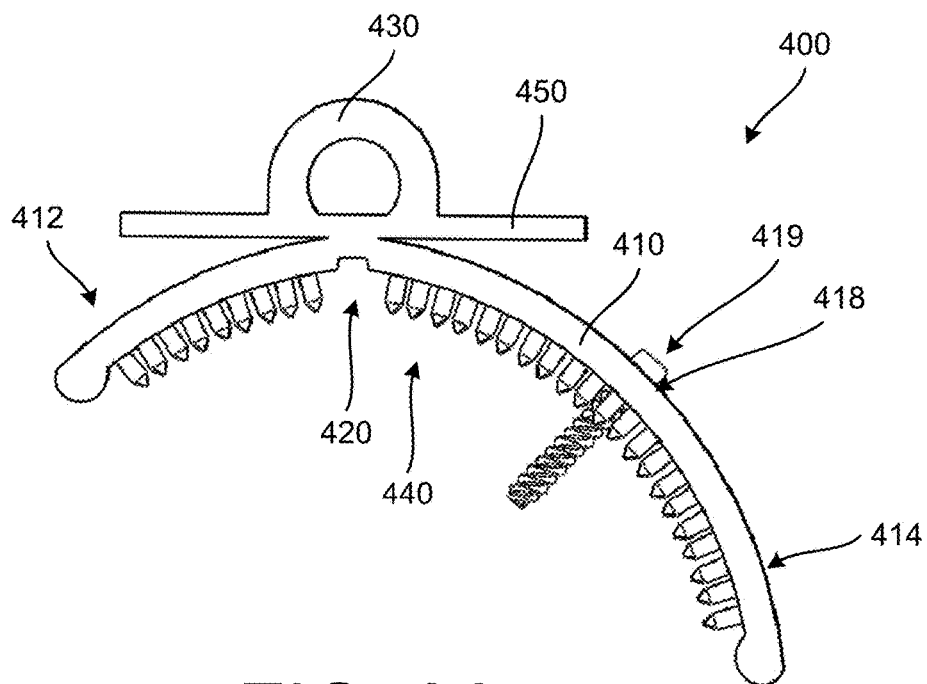
FIGS. 9A through 9D are a diagram that illustrate yet another variation of the vertebral attachment device shown in FIGS. 4A through 8.
Figure 9B:
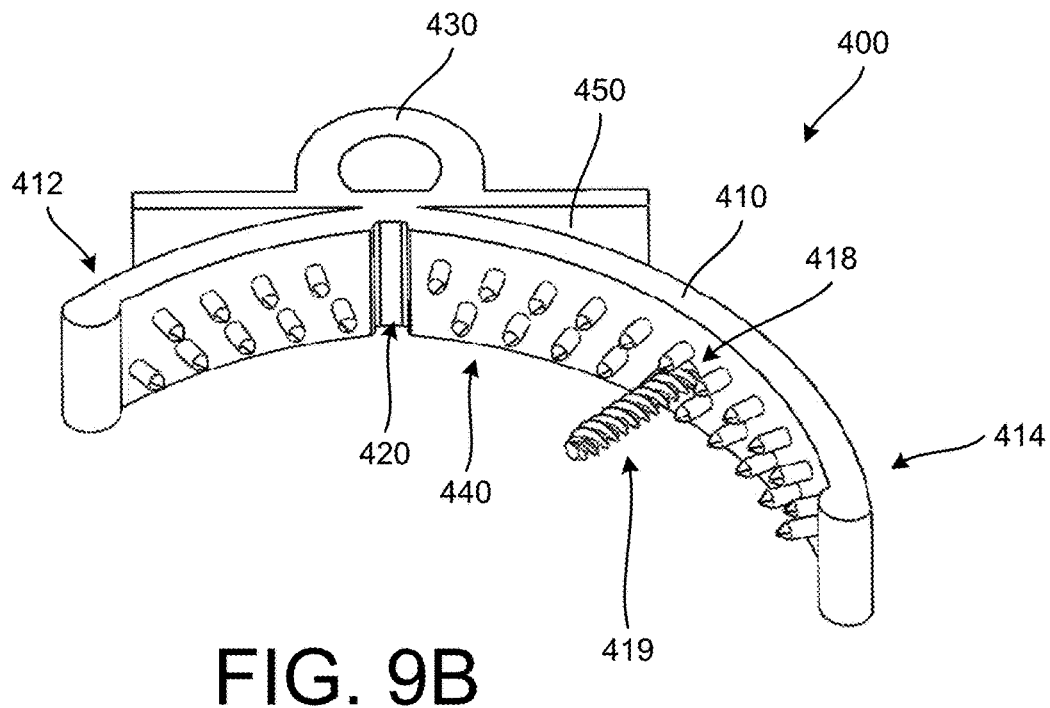
Figure 9C:
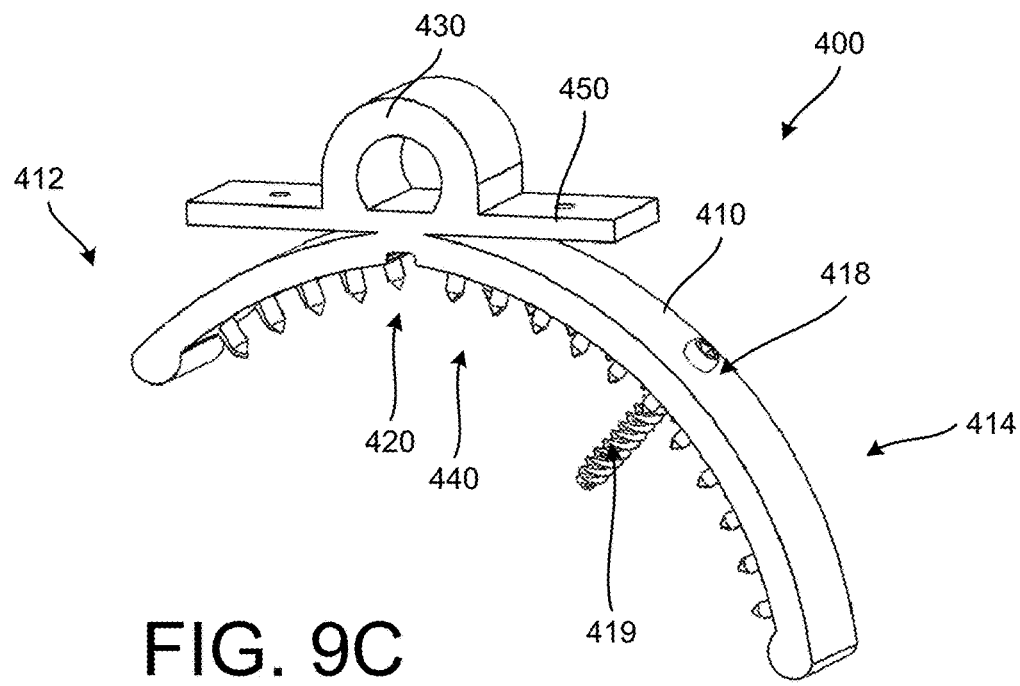
Figure 9D:
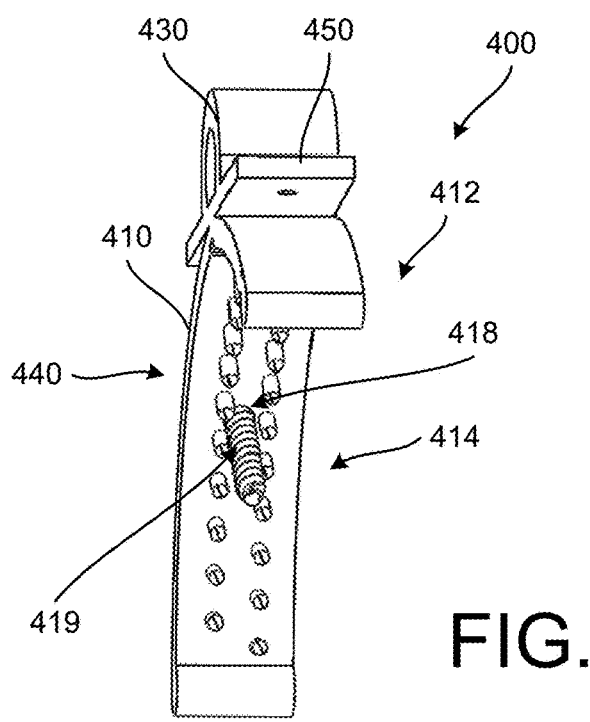

FIG. 8 is a diagram that illustrates another variation of the vertebral attachment device 400 shown in FIGS. 4A through 7. As shown in FIG. 8, the locking mechanism 450 and the coupling mechanism 430 are separate components that are each directly attached to the attachment member 410. In this implementation, the locking mechanism 450 is approximately aligned with the flex structure 420. In this implementation, both the locking mechanism 450 and the coupling mechanism 430 are offset (e.g., having a central portion not aligned along) from a line C1 bisecting the attachment member 410. In some implementations, the locking mechanism 450 can be separate from the coupling mechanism 430 so that a peripheral device coupled to the coupling mechanism 430 may not interfere with insertion of vertebral attachment device 400, with an anatomical portion of a body of a patient, with the locking mechanism 450, and/or so forth.

FIGS. 9A through 9D are a diagram that illustrate yet another variation of the vertebral attachment device 400 shown in FIGS. 4A through 8. In FIGS. 9A through 9D not all of the components of the vertebral attachment device 400 are labeled.

As shown in FIGS. 9A through 9D, a screw 419 is disposed within an opening 418 within the arm portion 414 (which is longer than arm portion 412). In this implementation, the screw 419 protrudes in the same direction as the anchor members 440. The screw 419 has a length that is greater than a length of the anchor members 440.

In this implementation, the opening 418 through which screw 419 is disposed is between the rows of anchor members 440. Also, the screw 419 is approximately aligned within a middle of a width of the attachment member 410. In some implementations, the screw 419 may not be disposed in between the rows of anchor members 440 (or within a middle of a width of the arm portions 412, 414 of the attachment member 410).

Although not shown, in some implementations, the screw 419 can be disposed within an opening of the arm portion 412 rather than the arm portion 414. In some implementations, an additional screw can be disposed within an opening of the arm portion 412. In such implementations, the additional screw can have a same length or a different length then the screw 419.

As noted above, the screw 419 may be used in conjunction with the vertebral attachment device 400 to provide more secure attachment, specifically increasing the resistance of the vertebral attachment device to shear motion. The compliancy and design of the vertebral attachment device 400 is such that the screw 419 can be much smaller in diameter than known screws for spinal attachment. In this regard, the screw 419 can be much less destructive and damaging than known screws.

Figure 10A:
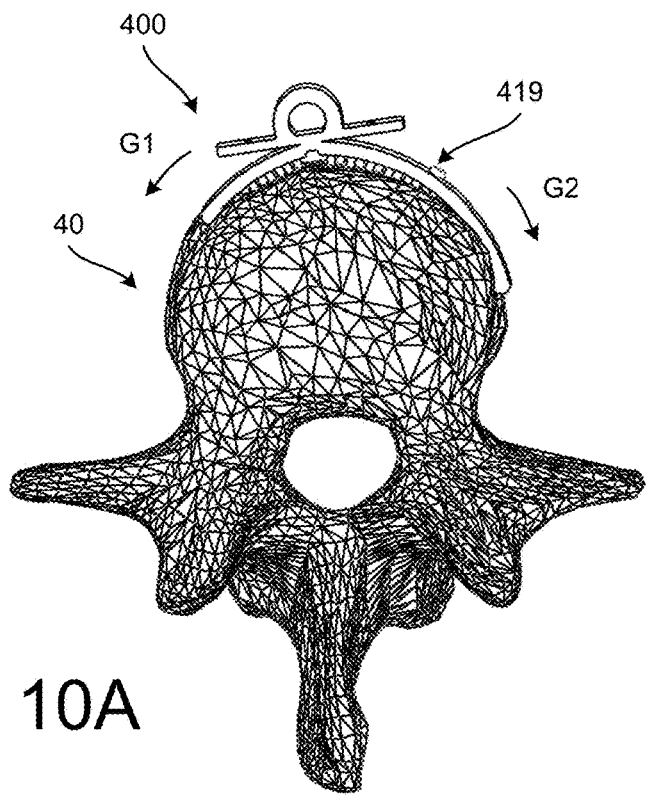
FIGS. 10A through 10C are various perspective views that illustrate the vertebral attachment device shown in FIGS. 9A through 9D coupled to a vertebrae.
Figure 10B:
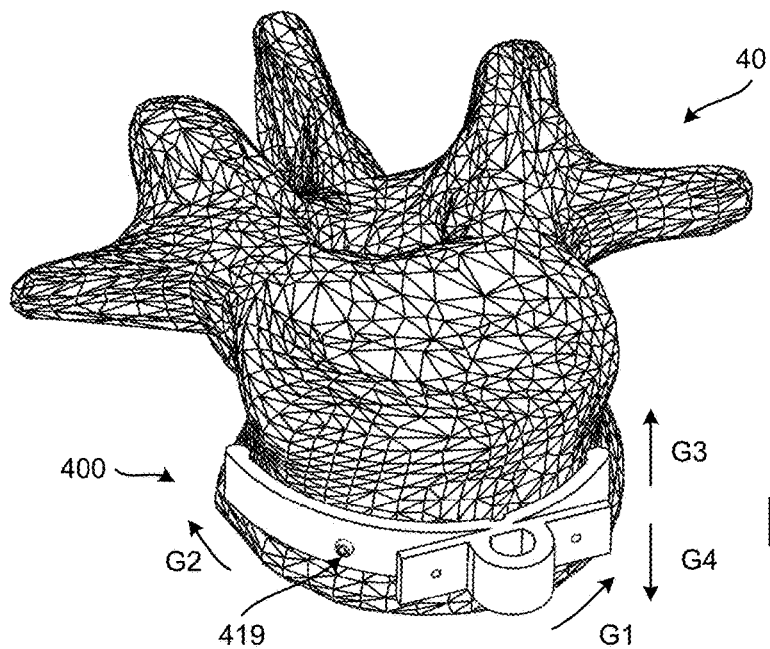
Figure 10C:
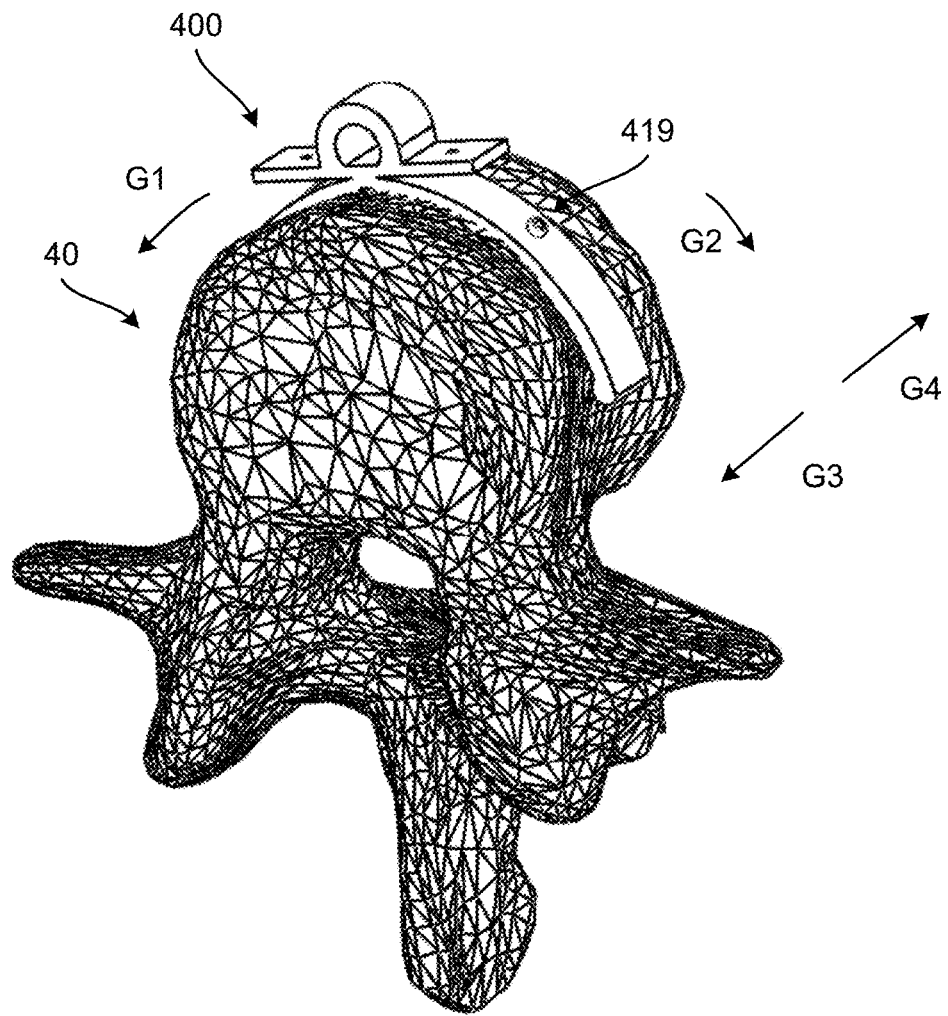

FIGS. 10A through 10C are various perspective views that illustrate the vertebral attachment device 400 shown in FIGS. 9A through 9D coupled to a vertebra 40. In this implementation, the screw 419 can be engaged with (e.g., can be in contact) with the vertebra 40 to prevent the vertebral attachment device 400 from moving (e.g., sliding) in an undesirable fashion along directions G1 or G2 shown in FIG. 10A through 10C or along directions G3 or G4 shown in FIGS. 10B and 10C.

Figure 12:
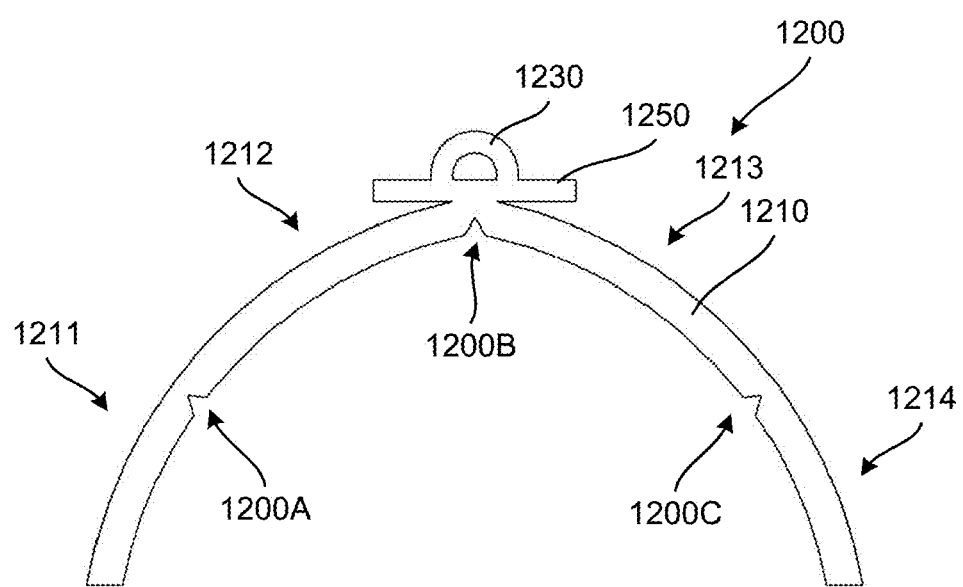
FIG. 12 is a diagram that illustrates a vertebral attachment device that has an attachment member that includes multiple flex structures.

FIG. 12 is a diagram that illustrates a vertebral attachment device 1200 that has a coupling mechanism 1230, a locking mechanism 1250, and an attachment member 1210 that includes multiple flex structures 1200A, 1200B, and 1200C. This vertebral attachment device 1200 can be an implementation of the vertebral attachment devices described above and can include (or can be included in) any of the features described herein.

The anchor members are not shown in FIG. 12. In this implementation, the multiple flex structures 1200A, 1200B, 1200C are symmetrically spaced along the attachment member 1210. In some implementations, one or more of the multiple flex structures 1200A, 1200B, 1200C may not be symmetrically spaced along the attachment member 1210.

The flex structures 1200A, 1200B, 1200C are used to define 4 arm portions 1211, 1212, 1213, 1214 of the attachment member 1210. In this implementation, the arm portions 1212 and 1213 have the same length and the arm portions 1211 and 1214 have the same length. In some implementations, the flex structures can be at different locations along the attachment member 1210 so that the arms portions 1211, 1212, 1213, 1214 have the same length or can have different lengths than shown.

In some implementations, the flex structures 1200A, 1200B, 1200C can be the same (e.g., same shape, same depth, same dimensions). In some implementations, one or more of the flex structures 1200A, 1200B, 1200C can be different than the other of the flex structures 1200A, 1200B, 1200C. In some implementations, the vertebral attachment device 1200 can have more or less flex structures than shown.

Figure 13:
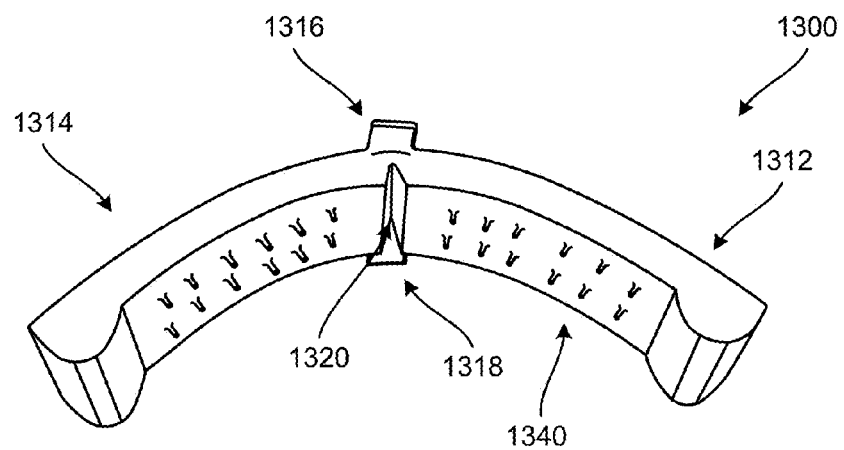
FIGS. 13 and 14 illustrate views of another vertebral attachment device.
Figure 14:
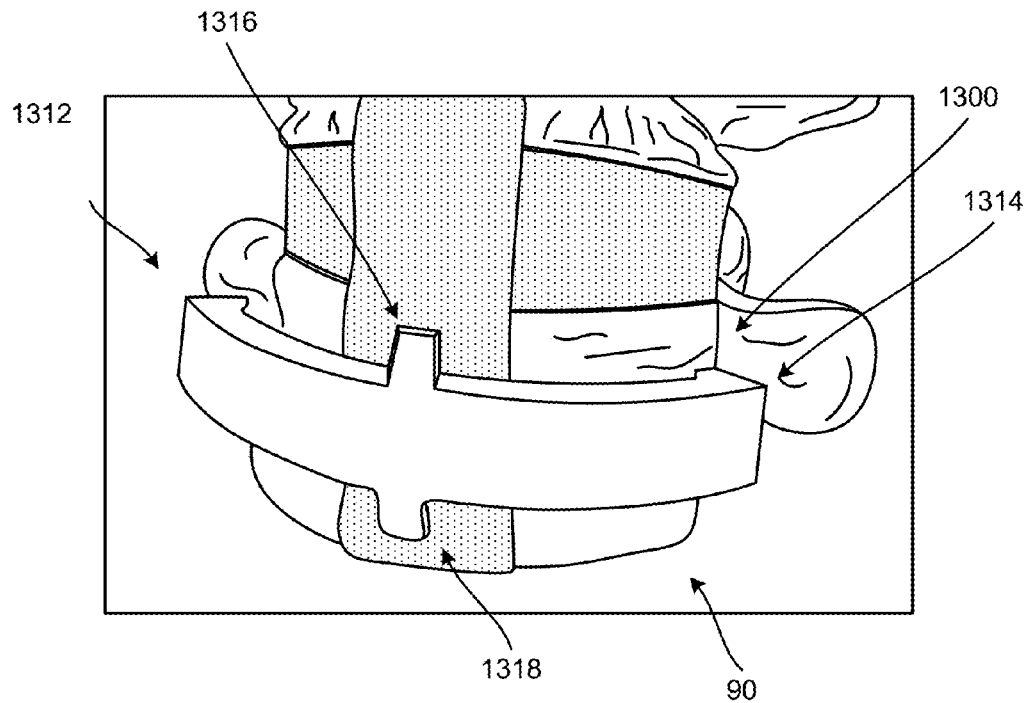

FIGS. 13 and 14 illustrate views of another vertebral attachment device 1300. FIG. 14 illustrates the vertebral attachment device 1300 coupled to a vertebra 90. The vertebral attachment device 1300 can be a variation of the vertebral attachment device 100 shown in FIGS. 1A and 1B.

The vertebral attachment device 1300 can be a compliant structure that can be configured to attach to the anterior side of the vertebra 90. The vertebral attachment device 1300 includes at least two main curved arm portions 1312 and 1314 that wrap around the sides of the vertebra 90. The at least two arm portions 1312 and 1314 can be, for example, rigid and connected via, for example, a small-length flexural pivot. Due to this design, the arm portions 1312 and 1314 can accommodate a wide variation in vertebral body dimensions and/or morphology. In some implementations, at least two smaller arm portions 1316 and 1318 (which are curved) are positioned on the superior and/or inferior sides of the vertebral attachment device 1300. These at least two smaller arm portions 1316, 1318 can provide an extra attachment to further secure the vertebral attachment device 1300.

In this implementation, the arm portions 1316, 1318 are aligned orthogonal to the arm portions 1312, 1314. In some implementations, the arm portions 1316, 1318 are not aligned orthogonal to the arm portions 1312, 1314. In some implementations, one or more of the arm portions 1316, 1318 and/or one of more of the arm portions 1312, 1314 may not be curved.

The at least two main arm portions 1312, 1314 may have a series of (or a single) anchor members 1340 (e.g., needle-like structures) that can pierce into (or be otherwise coupled to) the bone and provide a more secure attachment.

Figure 15:
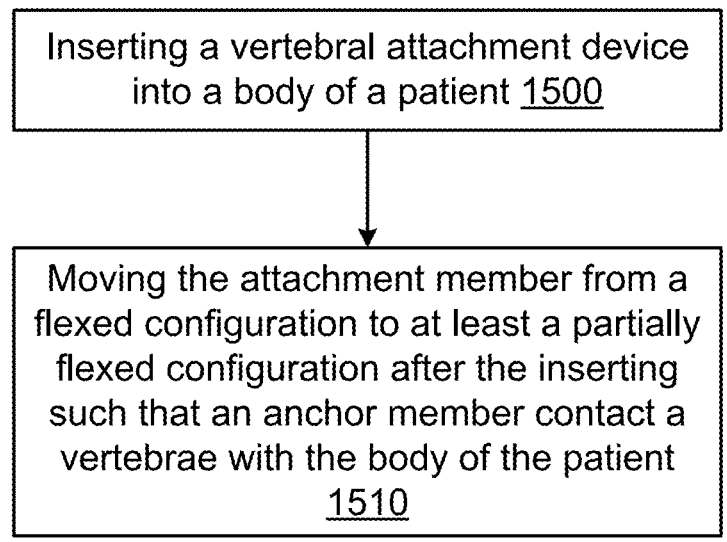
FIG. 15 is a flowchart that illustrates a process for using a vertebral attachment device.

FIG. 15 is a flowchart that illustrates a process for using a vertebral attachment device. As shown in FIG. 15, the process can include inserting a vertebral attachment device into a body of a patient (block 1500). The vertebral attachment device can include an attachment member having a curved shape defining a concave surface, a flex structure included in the attachment member, and an anchor member coupled to the attachment member and protruding from the concave surface. The method can also include moving the attachment member from a flexed configuration to at least a partially flexed configuration after the insertion such that the anchor member contacts a vertebra within the body of the patient. In some implementations, the anchor member can contact an anterior portion of the vertebra. In some implementations, moving the attachment member to a flexed configuration is performed before the inserting. In some implementations, moving the attachment member to a flexed configuration is performed after the inserting.

In some implementations, a structured design process can be used to identify a design. A set of desired characteristics can be developed based on desired functions for the device. These functions can satisfy both medical device attachment and/or biomechanical testing attachment requirements. At least five main categories can be established to fill the desired characteristics: how the device would interface with the body, reusability, material properties, in vivo considerations, ex vivo considerations, and/or so forth. In some implementations, a plethora of potential attachment methods can be evaluated and rated based on how they can perform compared to the previously mentioned categories. Several options can be chosen and implementations can be constructed to determine the physical viability of each option.

In some implementations, following conceptual device design, at least some of the concepts can be dimensioned and analyzed using a pseudo-rigid body modeling approach, in concert with a stress analysis of the external loading conditions imposed during use as an implanted medical device, as well as during ex vivo mechanical loading. In some implementations, two external forces can be applied to the device. The first force $F_c$ represents the compressive force that the spine experiences due to the weight of the body. This force can be divided by W, the distance from the hinge (or flex structure) to the top of the arms (or arm portions). The other external force $F_a$ is the applied force on the spine that it experiences due to the spine motion. At least these two forces are related to the force N required to clamp the spine by $$\frac{F_c}{W} + F_a = N\mu$$

where μ is the friction coefficient between the device and the vertebral bone. This coefficient can, in some implementations, be determined experimentally. The vertebral attachment device force N can then be used in a beam stress equation to determine the ideal geometry of the vertebral attachment device for a given material.

$$\sigma = \frac{Ndy}{I}$$

In this equation σ is the ultimate stress for a chosen material, d can be the moment arm for N (i.e., the perpendicular distance from the clamping force point of application to the central pivot (or flex structure) of the vertebral attachment device), y is the distance $h_o/2$ from the neutral axis, and I is the second moment of inertia for the tapered hinge. Since the hinge can be tapered in some implementations, I can account for the variable cross-section. Thus $$I = \frac{t\left(\frac{x}{l}(h - h_o) + h_o\right)^3}{12}$$

where x represents distance from the central pivot of the vertebral attachment device, t is the thickness of the vertebral attachment device, h is the final height of the tapered hinge, and $h_o$ is the initial height of the tapered hinge. Due to the nature of these equations multiple solutions for geometrical values can be calculated. Based on the design and stress analyses, suitable versions of the vertebral attachment device are reasonable for a variety of potential material choices.

In one general aspect, a vertebral attachment device can include an attachment member having a curved shape defining a concave surface, a flex structure included in the attachment member, and an anchor member coupled to the attachment member and protruding from the concave surface. The general aspect can include any combination of the following elements.

In some implementations, the attachment member has a first arm portion and a second arm portion. In some implementations, the attachment member has a first arm portion disposed on one side of the flex structure and a second arm portion disposed on a second side of the flex structure. In some implementations, the attachment member has a first arm portion having a first length from an end of the first arm portion and the flex structure, the attachment member has a second arm portion having a second length from an end of the second arm portion and the flex structure that is different from the first length.

In some implementations, the flex structure defines a recess in the attachment member. In some implementations, the flex structure is at a location offset from a center of the curved shape of the attachment member. In some implementations, the flex structure is included on a same side of the attachment member as the anchor member. In some implementations, the attachment member has a length greater than a width of the attachment member.

In some implementations, the attachment member defines a convex surface on a side of the attachment member opposite a side of the concave surface. The vertebral attachment device can also include a coupling mechanism coupled to the convex surface of the attachment member. In some implementations, the coupling mechanism defines an opening.

In some implementations, the vertebral attachment device can include a locking mechanism. In some implementations, the locking mechanism a locking arm. In some implementations, the attachment member defines a convex surface on a side of the attachment member opposite a side of the attachment member defining the concave surface. The curved shape of the attachment member can define a curvature. The vertebral attachment device can include a coupling mechanism coupled to the convex surface of the attachment member such that a line intersecting a center of the curvature and the flex structure also intersects the coupling member.

In some implementations, the attachment member defines a convex surface on a side of the attachment member opposite a side of the attachment member defining the concave surface. The curved shape of the attachment member can define a curvature. The vertebral attachment device can include a coupling mechanism coupled to the convex surface of the attachment member such that a line intersecting a center of the curvature and the flex structure does not intersect the coupling member.

In some implementations, the attachment member is biased to the curved shape defining the concave surface. The attachment member can have an arm portion configured to be moved such that a radius of curvature of the concave surface is increased. In some implementations, the anchor member protrudes from the concave surface in a first direction. The attachment member can have an arm portion configured to be moved in a second direction substantially opposite the first direction.

In some implementations, the anchor member is a first anchor member that has a diameter. The vertebral attachment device can include a second anchor member adjacent the first anchor member without an intervening anchor member. The first anchor member can be separated from the second anchor member by a distance greater than the diameter. In some implementations, the distance is at least 2 times the diameter. In some implementations, the vertebral attachment is monolithically formed.

In another general aspect, a method can include inserting a vertebral attachment device into a body of a patient. The vertebral attachment device can include an attachment member having a curved shape defining a concave surface, a flex structure included in the attachment member, and an anchor member coupled to the attachment member and protruding from the concave surface. The method can include moving the attachment member from a flexed configuration to at least a partially flexed configuration after the inserting such that the anchor member contacts a vertebra within the body of the patient. The general aspect can include any combination of the following elements.

In some implementations, the anchor member contacts an anterior portion of the vertebra. In some implementations, the moving the attachment member to a flexed configuration is performed before the inserting. In some implementations, the moving the attachment member to a flexed configuration is performed after the inserting.

The disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the embodiments.

It will also be understood that when an element, such as a layer, a region, or a substrate, is referred to as being on, connected to, electrically connected to, coupled to, or electrically coupled to another element, it may be directly on, connected or coupled to the other element, or one or more intervening elements may be present. In contrast, when an element is referred to as being directly on, directly connected to or directly coupled to another element or layer, there are no intervening elements or layers present. Although the terms directly on, directly connected to, or directly coupled to may not be used throughout the detailed description, elements that are shown as being directly on, directly connected or directly coupled can be referred to as such. The claims of the application may be amended to recite exemplary relationships described in the specification or shown in the figures.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically. Accordingly, a singular form may, unless definitely indicating a particular case in terms of the context, include a plural form. Spatially relative terms (e.g., over, above, upper, under, beneath, below, lower, and so forth) are intended to encompass different orientations of the device in use or operation in addition to the orientation depicted in the figures. In some implementations, the relative terms above and below can, respectively, include vertically above and vertically below. In some implementations, the term adjacent can include laterally adjacent to or horizontally adjacent to.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the implementations. It should be understood that they have been presented by way of example only, not limitation, and various changes in form and details may be made. Any portion of the apparatus and/or methods described herein may be combined in any combination, except mutually exclusive combinations. The implementations described herein can include various combinations and/or sub-combinations of the functions, components and/or features of the different implementations described.

What is claimed is:

1. A vertebral attachment device, comprising:
an attachment member having a curved shape defining a concave surface, the attachment member having an arm portion;
a flex structure included in the attachment member, the attachment member being monolithically formed, the flex structure defining a recessed portion having a thickness less than a thickness of the arm portion of the attachment member, the attachment member being biased about the flex structure to the curved shape defining the concave surface, the attachment member configured to be moved such that a radius of curvature of the concave surface is increased; and
an anchor member coupled to the attachment member and protruding from the concave surface.

2. The vertebral attachment device of claim 1, wherein the arm portion is a first arm portion disposed on one side of the flex structure, the attachment member has a second arm portion disposed on a second side of the flex structure.

3. The vertebral attachment device of claim 1, wherein the arm portion is a first arm portion having a first length from an end of the first arm portion and the flex structure, the attachment member has a second arm portion having a second length from an end of the second arm portion and the flex structure that is different from the first length.

4. The vertebral attachment device of claim 1, wherein the flex structure is at a location offset from a center of the curved shape of the attachment member.

5. The vertebral attachment device of claim 1, wherein the flex structure is included on a same side of the attachment member as the anchor member.

6. The vertebral attachment device of claim 1, wherein the attachment member has a length greater than a width of the attachment member.

7. The vertebral attachment device of claim 1, wherein the attachment member defines a convex surface on a side of the attachment member opposite a side of the concave surface,
the vertebral attachment device further comprising:
a coupling mechanism coupled to the convex surface of the attachment member.

8. The vertebral attachment device of claim 7, wherein the coupling mechanism defines an opening.

9. The vertebral attachment device of claim 1, further comprising:
a locking mechanism.

10. The vertebral attachment device of claim 9, wherein the locking mechanism a locking arm.

11. The vertebral attachment device of claim 1, wherein the attachment member defines a convex surface on a side of the attachment member opposite a side of the attachment member defining the concave surface, the curved shape of the attachment member defining a curvature,
the vertebral attachment device further comprising:
a coupling mechanism coupled to the convex surface of the attachment member such that a line intersecting a center of the curvature and the flex structure also intersects the coupling mechanism.

12. The vertebral attachment device of claim 1, wherein the arm portion is a first arm portion, the flex structure is disposed between the first arm portion of the attachment member and a second arm portion of the attachment member.

13. The vertebral attachment device of claim 1, wherein the arm portion is a first arm portion, the thickness of the recessed portion of the flex structure is less than a thickness of a second arm portion of the attachment member.

14. The vertebral attachment device of claim 1, wherein the attachment member defines a convex surface on a side of the attachment member opposite a side of the attachment member defining the concave surface, the curved shape of the attachment member defining a curvature, the vertebral attachment device further comprising:
a coupling mechanism coupled to the convex surface of the attachment member such that a line intersecting a center of the curvature and the flex structure does not intersect the coupling mechanism.

15. The vertebral attachment device of claim 1, wherein the anchor member protrudes from the concave surface in a first direction, the attachment member having a first arm portion configured to be moved in a second direction substantially opposite the first direction.

16. The vertebral attachment device of claim 1, wherein the anchor member is a first anchor member that has a diameter, the vertebral attachment device further comprising:
a second anchor member adjacent the first anchor member without an intervening anchor member, the first anchor member being separated from the second anchor member by a distance greater than the diameter.

17. The vertebral attachment device of claim 16, wherein the distance is at least 2 times the diameter.

18. A method, comprising:
inserting a vertebral attachment device into a body of a patient, the vertebral attachment device including:
an attachment member having a first arm portion and a second arm portion, each of the first arm portion and the second arm portion having a curved shape defining a concave surface,
a flex structure included in the attachment member, the flex structure defining a recessed portion, the recessed portion having a thickness less than a thickness of the first arm portion, the first arm portion and the second arm portion of the attachment member each being biased about the flex structure to the curved shape defining the concave surface, and
an anchor member coupled to the attachment member and protruding from the concave surface; and
moving the first arm portion and the second arm portion of the attachment member from a flexed configuration to at least a partially flexed configuration after the inserting such that the anchor member contacts a vertebra within the body of the patient, the first arm portion and the second arm portion of the attachment member being moved such that a radius of curvature of each of the first arm portion and the second arm portion is increased.

19. The method of claim 18, wherein the anchor member contacts an anterior portion of the vertebra.

20. The method of claim 18, wherein the moving the attachment member to a flexed configuration is performed before the inserting.

21. The method of claim 18, wherein the moving the attachment member to a flexed configuration is performed after the inserting.

22. A vertebral attachment device, comprising:
an attachment member having a first arm portion and a second arm portion, each of the first arm portion and the second arm portion having a curved shape defining a concave surface;
a flex structure included in the attachment member, the flex structure defining a recessed portion in the attachment member, the attachment member being biased about the flex structure and configured to be moved such that a radius of curvature of each of the first arm portion and the second arm portion is increased, the recessed portion having a thickness less than a thickness of the first arm portion, the first arm portion being on a first side of the flex structure and the second arm portion being on a second side of the flex structure; and
an anchor member coupled to the attachment member and protruding from the concave surface.

23. The vertebral attachment device of claim 22, wherein the vertebral attachment device is monolithically formed.

* * * * *